United States Patent
Dutta et al.

(10) Patent No.: US 7,923,054 B2
(45) Date of Patent: Apr. 12, 2011

(54) FUNCTIONAL POROUS SUBSTRATES FOR ATTACHING BIOMOLECULES

(75) Inventors: Anit Dutta, Wilmington, DE (US); Heidi Flannery, Abingdon, MD (US); William P. Mortimer, Jr., North East, MD (US)

(73) Assignee: Gore Enterprise Holdings, Inc., Newark, DE (US)

( * ) Notice: Subject to any disclaimer, the term of this patent is extended or adjusted under 35 U.S.C. 154(b) by 838 days.

(21) Appl. No.: 11/407,882

(22) Filed: Apr. 19, 2006

(65) Prior Publication Data
US 2007/0248985 A1   Oct. 25, 2007

(51) Int. Cl.
*G01N 1/28* (2006.01)
(52) U.S. Cl. ............... 427/2.11; 435/287.1; 435/286.5; 436/528
(58) Field of Classification Search .................. None
See application file for complete search history.

(56) References Cited

U.S. PATENT DOCUMENTS

| | | | |
|---|---|---|---|
| 3,953,566 A | 4/1976 | Gore | 264/288 |
| 4,187,390 A | 2/1980 | Gore | 174/102 |
| 4,340,480 A | 7/1982 | Pall et al. | 210/490 |
| 5,130,024 A | 7/1992 | Fujimoto et al. | 210/500.36 |
| 5,270,193 A * | 12/1993 | Eveleigh | 435/181 |
| 5,420,047 A | 5/1995 | Brandt et al. | 435/7.9 |
| 5,614,099 A | 3/1997 | Hirose et al. | 210/653 |
| 5,627,079 A | 5/1997 | Gardella, Jr. et al. | 436/525 |
| 5,843,789 A | 12/1998 | Nomura et al. | 436/134 |
| 5,897,955 A | 4/1999 | Drumheller | 428/422 |
| 5,902,745 A * | 5/1999 | Butler et al. | 435/297.2 |
| 6,207,369 B1 | 3/2001 | Wohlstadter et al. | 435/6 |
| 6,403,368 B1 | 6/2002 | Jan et al. | 435/287 |
| 6,734,012 B2 | 5/2004 | Andreoli et al. | 435/287 |
| 6,750,023 B2 | 6/2004 | Tanner et al. | 435/6 |
| 6,790,613 B1 | 9/2004 | Shi et al. | 435/6 |
| 2001/0019765 A1* | 9/2001 | Kiuchi et al. | 428/345 |
| 2002/0004126 A1* | 1/2002 | Honda et al. | 428/220 |
| 2002/0019015 A1 | 2/2002 | Lahiri et al. | 435/7.9 |
| 2002/0031628 A1* | 3/2002 | Zumbrum et al. | 428/36.9 |
| 2002/0076709 A1 | 6/2002 | Hevesi et al. | 435/6 |
| 2002/0081715 A1 | 6/2002 | Tashiro et al. | 435/287.2 |
| 2002/0086307 A1 | 7/2002 | Amin et al. | 436/6 |
| 2002/0119559 A1 | 8/2002 | Andreoli et al. | 435/6 |
| 2002/0142339 A1 | 10/2002 | Bardhan et al. | 435/6 |
| 2003/0036085 A1 | 2/2003 | Salinaro et al. | 435/6 |
| 2003/0049435 A1* | 3/2003 | Haddad et al. | 428/328 |
| 2003/0068621 A1 | 4/2003 | Briggs | 435/6 |
| 2003/0138853 A1 | 7/2003 | Lahiri et al. | 435/7.1 |

(Continued)

FOREIGN PATENT DOCUMENTS

JP        08/150101        3/1995

(Continued)

OTHER PUBLICATIONS

Supplementary European Search Report for EP 07 87 2144 dated Apr. 29, 2010.

(Continued)

*Primary Examiner* — N. C. Yang
(74) *Attorney, Agent, or Firm* — Allan M. Wheatcraft

(57) ABSTRACT

A substrate comprising a microporous microstructure, an interlayer over at least a portion of the microstructure and a functional layer attached to the interlayer, the functional layer having functional sites with a density of at least 50 nanomoles/cm$^2$.

50 Claims, 5 Drawing Sheets

U.S. PATENT DOCUMENTS

| | | |
|---|---|---|
| 2003/0219816 A1 | 11/2003 | Solomon et al. ............... 435/6 |
| 2003/0224160 A1* | 12/2003 | Murakami et al. ............ 428/343 |
| 2003/0235824 A1 | 12/2003 | Trulson et al. ................ 435/6 |
| 2004/0043508 A1 | 3/2004 | Frutos et al. ................. 436/518 |
| 2004/0081886 A1 | 4/2004 | Zuckerbrod et al. .......... 429/144 |
| 2004/0115721 A1 | 6/2004 | Mao et al. ..................... 435/6 |
| 2004/0137608 A1 | 7/2004 | Garzon et al. ............. 435/287.2 |
| 2004/0146920 A1 | 7/2004 | Lee et al. ..................... 435/6 |
| 2004/0152081 A1 | 8/2004 | Leproust et al. ............... 435/6 |
| 2004/0157320 A1 | 8/2004 | Andreoli et al. ........... 435/287.2 |
| 2004/0209269 A1 | 10/2004 | Dugas et al. .................. 435/6 |
| 2004/0240137 A1 | 12/2004 | Fisher-Fruhholz et al. .... 361/115 |
| 2004/0241751 A1 | 12/2004 | Wagnet et al. ................ 435/7.1 |
| 2005/0064431 A1 | 3/2005 | Leon et al. .................... 435/6 |
| 2005/0079506 A1 | 4/2005 | Leon et al. .................... 435/6 |
| 2005/0095602 A1 | 5/2005 | West et al. |
| 2005/0149175 A1* | 7/2005 | Hunter et al. ................ 623/1.42 |
| 2006/0024347 A1* | 2/2006 | Zamora et al. ............... 424/423 |
| 2006/0134695 A1* | 6/2006 | Quinn ........................... 435/7.1 |
| 2006/0160120 A1 | 7/2006 | Lee et al. ...................... 435/6 |

FOREIGN PATENT DOCUMENTS

| | | |
|---|---|---|
| WO | WO 00/04382 | 1/2000 |
| WO | WO 00/33078 | 6/2000 |
| WO | WO 00/65097 | 11/2000 |
| WO | WO 01/66244 A1 | 9/2001 |
| WO | WO 03/054551 | 7/2003 |
| WO | WO 2004/018623 | 3/2004 |

OTHER PUBLICATIONS

Gelest Inc.; "Silane Coupling Agents: Connecting Across Boundaries"Brochure, 2003.

Mark Schena, "Microarray Analysis", Published by John Wiley & Sons, Inc., 2003.

Edited by Ulrike A. Nuber, "DNA Microarrays", Published by Taylor & Fracis Group 2005, pp. 210 and 211.

Tim Studt, "Microarrays Move From Discovery to Diagnostics", R&D Magazine, Sep. 2002, vol. 44, Issue 9, p. 22, 2p, 1 diagram.

ASTM Desingation: F 31 6 -03 "Standard Test Methods for Pore Size Characteristics of Membrane Filters by Bubble Point and Mean Flow Pore Test", Apr. 2003.

V.K. Sarin, S. B. H. Kent, J. P. Tam, and R. B. Merrifield, "Quantitative Monitoring of Solid Phase Peptide Synthesis by the NinHydrin Reaction", The Rockefeller Universtiy, New York, NY 10021, pp. 221-224, 1981.

Samuel D. Conzone and Carol G. Pantano, "Glass Slides to DNA microarrays", Materials Today, Mar. 2004.

Peter Gwynne and Gary Heebner, "DNA Chips and Microarrays Part 1" Science Magazine, 2001.

Pierre Baldi and G. Wesley Hatfield, "DNA Microarrays and Gene Expression" 2002 Chapter 2, "DNA array formats" p. 7-13.

* cited by examiner

Scatter Plot of Normalized Signal Intensity UG

FUNCTIONAL POROUS SUBSTRATES FOR ATTACHING BIOMOLECULES

FIELD OF THE INVENTION

This invention relates to functional porous substrates and, more particularly, to such substrates used in a microarray application for detection of biomolecules.

BACKGROUND OF THE INVENTION

Owing to their high throughput screening capability, microarrays have become an essential tool for the healthcare and pharmaceutical industries where researchers are working to diagnose disease or discover new drugs. Moreover, agriculture and homeland defense firms are utilizing microarrays to uncover information regarding the presence of harmful pathogenic bacteria. Such simultaneous screening is possible by printing many microscopic spots, typically 10-250 µm in size, of biological molecules (i.e., biomolecules such as nucleic acid fragments, antibodies, peptides, proteins, pathogens, cells and the like) as probes onto the same substrate to form a microarray. A high density microarray developed for research purposes typically comprises between 1000 to 50000 probe spots arranged in a predetermined regular pattern on a substrate, thus leading to a spot density of about 50 spots/cm$^2$ to 2500 spots/cm$^2$. The dimension of the substrate can vary, but generally the substrate is the size of a 1 inch by 3 inch microscope slide. It is critical that the substrate surface be reactive and capable of binding probe bio-molecules of known sequence. In use, the microarray is hybridized with target bio-molecules of unknown sequence in order to simultaneously detect the response of the target with the different probes spotted on the array surface. Typically, targets are labeled with fluorescent dyes and fluorescence based detection techniques are most commonly used to quantify the response of the target biomolecule to the probes following hybridization. The composite quantitative response of the target to all the probes spotted on the microarray substrate is the data resulting from the microarray experiment.

Microarray experiments can be employed to detect the expression levels of various genes or proteins for a given organism (i.e. human, mouse, plant, bacteria, etc). Highly expressed genes or proteins are much easier to detect because their concentration in a given sample is often the greatest. However, when expression levels are low or samples are scarce, sensitive and reliable detection technology becomes critical. This type of detection technology is increasingly important for studying protein-protein interactions or protein biochemical activity since the concentration of proteins can not be amplified via enzymatic reactions such as the polymerase chain reaction.

As a result, within the microarray industry, there is an overriding need for confident detection of low abundant protein and/or nucleic acids. When attempting to accurately measure or detect such low levels in a microarray experiment, it is imperative that researchers employ system components that maximize sensitivity and overall signal to noise ratio. A number of approaches can be employed to impact sensitivity and signal to noise ratio and three of the common ones are as follows: (1) improvements in the sensitivity or detection limits of scanning devices, (2) increased amplification of the fluorescent signal via labeling methods, and (3) the employment of a highly sensitive substrate. The present invention focuses on enhancing signal to noise ratio through the employment of a highly sensitive microarray substrate.

An increase in signal strength can be achieved by increasing the number of binding sites per unit area (functional site density), which ultimately impacts the retention of immobilized bio-molecular probes and the emission of an increased signal when hybridized with fluorescently labeled target molecules. Signal clarity can also be enhanced through a reduction in the inherent auto-fluorescence of the materials and/or system used for detection. These approaches will ultimately influence the signal to noise ratio, either by increasing the signal strength, and/or reducing the noise. Several prior art approaches have been attempted.

Many common methods used to manufacture high density microarrays use non-porous, two-dimensional glass substrates containing functional sites for binding samples of interest. Glass is preferred because of its inertness and low inherent auto-fluorescence which contributes less noise to the signal being detected, usually measured by fluorescence-based techniques. Examples of such commercially available substrates are UltraGAPS II® slides (Corning Inc., Life Sciences, Oneonta, N.Y.), Nexterion® Slides (Schott North America, Inc., Louisville, Ky.), and Array-It® slides (Telechem International Inc., Sunnyvale, Calif.). One drawback to using non-porous glass is that the functional site density is quite low resulting in relatively weak signals, which makes it very difficult to detect the sample of interest, especially when trying to detect low expressing genes or proteins. This effect can be minimized by increasing the volume or concentration of the sample of interest, however, the approach can only be employed if a large enough sample is available. Often, researchers are highly limited by the quantity, concentration or volume of a given sample. A common approach to increasing functional site density has been through the use of porous substrates to increase the accessible surface area containing the functional sites. Tanner et al. (U.S. Pat. No. 6,750,023) teach a method of forming a functional material for attaching an array of biological or chemical analytes by applying an inorganic porous layer to an inorganic non-porous understructure.

Alternate approaches using organic polymers as functional materials have been attempted. Haddad et al. (WO 01/66244) teach making arrays utilizing textured non-porous functional materials created from oriented polymer films. Porous organic polymers have also been used in microarray substrates and examples of such commercially available materials are Vivid Microarray® Slides (Pall Corporation, East Hills, N.Y.) and CAST® slides (Schleicher & Schuell Biosciences, Inc., Keene, N.H.), both using porous nylon membranes.

Phase inversion is a common technique used to make microporous membranes from organic polymers. Use of such membranes as microarray substrates is described in detail in U.S. Patent Applications 2003/0219816 of Solomon et al and 2004/0157320 of Andreoli et al. A variety of microporous materials are discussed in the literature, with nylon and nitrocellulose being the most common. Nylon affords the benefits that it can be readily rendered microporous and has a natural affinity for DNA. Similarly, nitrocellulose is known to be effective in binding proteins. In the case of nylon and nitrocellulose, binding with DNA and/or proteins is reliant on the inherent functional groups present in the nylon or nitrocellulose polymer backbone. Consequently, the functional site density afforded by these materials is limited. Moreover, the pore size of phase inversion membranes may not be small enough to prevent lateral spot spreading which leads to crosstalk thereby limiting the array density. Another common problem with using organic polymers such as nylon or nitrocellulose resides with the fact that these materials possess inherently high auto-fluorescence. Since fluorescence-based detection is the most commonly used technique to quantify the hybridized target biomolecules, high auto-fluorescence contributes to increased background noise thereby adversely affecting the clarity of the fluorescent signal. Use of pigments such as carbon black has been shown to reduce the auto-fluorescence. Alternatively, as taught by Montagu (WO 2004/018623), the background noise can also be reduced by the use of a thin (less than about 5µ) functional material.

The need exists for an array substrate that can be easily fabricated, provides high functional site density and exhibits low auto-fluorescence to maximize signal to noise ratio. The present invention addresses all of these needs along with providing very high level of precision.

SUMMARY OF THE INVENTION

This invention provides a substrate comprising a microporous microstructure, an interlayer over at least a portion of the microstructure and a functional layer attached to the interlayer, the functional layer having functional sites with a density of at least 50 nanomoles/cm$^2$.

In another aspect, this invention provides a method of creating a functionalized article comprising the steps of (1) providing a microporous substrate having a microstructure, (2) depositing an interlayer over the microstructure, (3) and attaching a functional layer to the interlayer such that the article has a functional site density of at least 50 nanomoles/cm$^2$.

In yet another aspect, this invention provides an article comprising a support layer adjacent to a polytetrafluoroethylene substrate comprising a porous microstructure, an interlayer over at least a portion of the microstructure and a functional layer attached to the interlayer, the functional layer having functional sites with a density of at least 50 nanomoles/cm$^2$.

In still another aspect, this invention provides an article comprising a support layer adjacent to a polytetrafluoroethylene substrate comprising a porous microstructure, an interlayer over at least a portion of the microstructure and a functional layer attached to the interlayer, the functional layer having functional sites with a density of at least 50 nanomoles/cm$^2$, and a biomolecule attached to the functional material.

In a further aspect, this invention provides a method of measuring biomolecules comprising the steps of:
  (a) providing a support layer,
  (b) functionalizing the support layer,
  (c) disposing an adhesive on at least part of the support layer,
  (d) attaching a microporous polytetrafluoroethylene substrate having a node and fibril microstructure to the support layer via the adhesive,
  (e) functionalizing the microporous polytetrafluoroethylene substrate to form functional sites,
  (f) binding biomolecules to the functional sites, and
  (g) detecting the amount of biomolecules bound to the functionalized layer.

In a further aspect, this invention provides a method of preparing a microarray substrate comprising
  (a) providing a support layer,
  (b) optionally functionalizing said support layer,
  (c) disposing an adhesive on at least a part of said support layer,
  (d) attaching a microporous polytetrafluoroethylene substrate having a node and fibril microstructure to said support layer via said adhesive, and
  (e) functionalizing said microporous polytetrafluoroethylene substrate.

In another aspect, this invention provides a microarray substrate comprising an auto-fluorescence level less than 100 RFU at a wavelength of 635 µm and a functional site density greater than 50 nanomoles/cm$^2$.

In another aspect, this invention provides a microarray substrate comprising an auto-fluorescence level less than 1000 RFU at a wavelength of 532 µm and a functional site density greater than 50 nanomoles/cm$^2$.

In another aspect, this invention provides a microarray substrate comprising a signal to noise ratio for the Cy5 dye greater than 130, preferably greater than 150.

In another aspect, this invention provides a microarray substrate comprising a signal to noise ratio for the Cy3 dye is greater than 90, preferably greater than 110.

In another aspect, this invention provides a microarray substrate comprising a 1.5 fold precision level of at least 99%.

In another aspect, this invention provides a microarray substrate comprising a 1.2 fold precision level of at least 76%.

DETAILED DESCRIPTION OF THE INVENTION

Figure 1:
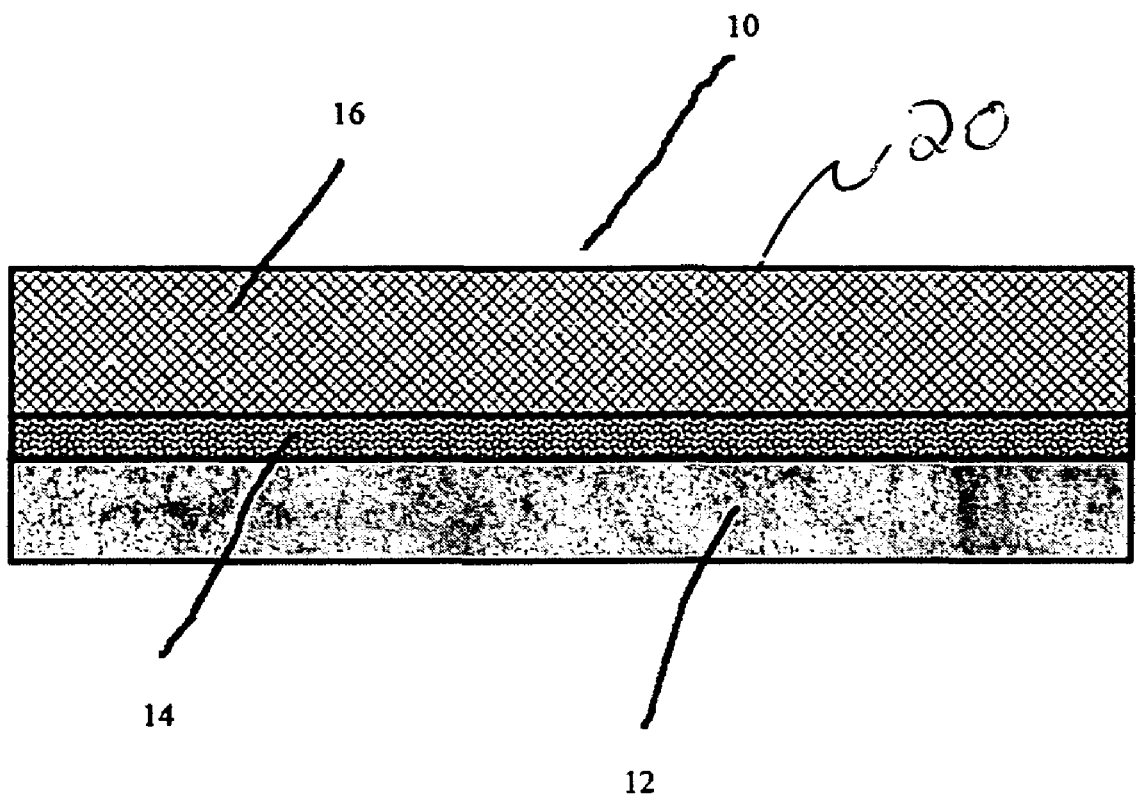
FIG. 1 is a transverse cross-sectional view of one end of an exemplary embodiment of the present invention.

The present invention is directed toward improved functional porous and microporous substrates with high functional group density and low auto-fluorescence which when used as a microarray substrate for bio-analytical detection provide heretofore unobtainable high signal-to-noise ratios with high precision level. These attributes derive from the unique combination of the selection of the porous and microporous materials and a method for functionalizing these materials. A microarray can be defined as a tool used to sift through and analyze the information contained within a genome. This tool contains different bio-molecular (nucleic acid, protein, cell, etc) probes that are chemically attached to a substrate, which can be a microchip, a glass slide or a microsphere-size bead. In the following discussion, "porous material" refers to a material with pores that extend through the entire cross-section thereby making the material permeable to fluids. Porous materials are typically characterized by the mean flow pore size. Alternatively, porous materials can be characterized by bubble point which is a measure of the maximum pore size. Both the mean flow pore size as well the bubble point can be measured by pressure-flow tests. Microporous materials are a subset of porous materials where the mean flow pore size is less than about 1 μm or the bubble point is greater than about 10 psi.

Porous materials of this invention are planar in nature and can be in the form of membranes or sheets. The porous substrates of this invention are permeable to fluids due to the presence of interconnecting pores that traverse the entire cross-section. The surface area of this microstructure is considerably higher than that of a non-porous material of equal volume. The present invention utilizes this microstructure and its attendant high surface area to volume ratio in creating the high functional density substrate. This internal surface area, better referred to as specific surface area, is related to the pore size of the porous material; the surface area increases as the average pore size of the material decreases. Typically, the specific surface area of the porous material is at least 0.1 $m^2/gm$ and preferably greater than 1 $m^2/gm$ and most preferably greater than 10 $m^2/gm$ as measured by standard gas adsorption techniques.

A "functional site" as used herein is a site located at either an external or internal surface of the porous substrate. Functional sites may be generated using the surface modification techniques described herein, and are useful for providing binding sites to which biomolecules may be attached. In certain preferred embodiments, the biomolecules that are attached to the functional sites serve as probe molecules to which a target biomolecule (typically an analyte in solution) can be bound, either covalently or non-covalently. Non-limiting examples of biomolecules contemplated by the invention include nucleic acids, oligonucleotides, and antibodies. "Functional group" as used herein is a group of atoms that reacts as a single unit and determines the properties of the functional site. A functional substrate is a porous substrate which has functional sites residing on the surface of its microstructure. The term "functionalize" refers to the process in which a functional group or groups is attached to the microstructure of a porous substrate.

Porous materials with their inherent high specific surface area to volume ratios offer more area for functionalization than non-porous substrates, such as non-porous glass. As mentioned earlier, use of such functional porous substrates for microarray applications have been taught in the prior art literature such as in U.S. Patent Application 2004/0157320 to Andreoli and to U.S. Pat. No. 6,750,023 to Tanner. Although these teachings take advantage of the increased internal surface area afforded by the porous microstructure, they rely on the inherent functional group density of the porous material for binding sites. For example, Andreoli teaches the use of porous nylon as the substrate with the functionality provided by the amide groups within the chemical structure of the nylon molecule. In comparison, Tanner teaches the use of porous glass but relies on the presence of surface hydroxyl group on the glass surface for subsequent functionalization through silane treatment.

The present invention takes a novel approach in creating the high functional density substrate for microarray application. The inventive approach starts with a porous material that does not rely on the inherent chemical nature of the material for creating the functional groups. Instead, the microstructure of the porous material is substantially coated with an intermediate layer containing a reactive functionality, such as hydroxyl functionality. The functional substrate is then created by reacting appropriate functional chemistries with the hydroxyl functionality of the intermediate layer. Functionalizing the substrate may thus include the step of depositing an interlayer over the porous micro-structure. In this approach, choice of the intermediate layer and not of the porous material, now controls the density of the functional groups. All prior art materials that were subsequently functionalized in accordance with these teachings of the present invention exhibited much higher functional group density.

The high functional density substrate of the present invention is obtained by starting with a porous material, preferably in a planar form such as membranes or sheets. The porous materials can be organic or inorganic in nature. Non-limiting examples of such organic porous materials could be porous sheets of ultahighmolecular weight polyethylene (UHMWPE) sold by Porex Corporation, polypropylene (PP) or polytetrafluoroethylene (PTFE) available from Small Parts, Incorporated (Miami Lakes, Fla.). Membranes made from organic polymers are typically microporous in nature and are available commercially. Examples of such materials are expanded PTFE (ePTFE) membranes available from W. L. Gore and Associates, nylon and polyvinylidenefluoride (PVDF) membranes available from Pall Corp under Biodyne™ and Biotrace™ brand names respectively, PP membrane available from Osmonics Inc. under PolySep™ brandname and PTFE membrane from Porex Corporation under Mupor™ brand name. Inorganic porous materials are typically available as rigid sheets. Such materials typically are obtained by sintering inorganic materials such as metals, ceramics and metal oxides. Porous glass is a common example of such sintered material and is available from companies such as R&H Filter company (Georgetown, Del.) or Advanced Glass & Ceramics (Holden, Mass.). Through proper choice of the porous material and subsequent functionalizing chemicals, the high functional density substrate of the present invention can also be made to have low auto fluorescence. Generally, materials devoid of conjugated bonds in their chemical structure exhibit low fluorescing properties. Examples of such porous materials are those that are made from materials such as PTFE, UHMWPE, PP, and glass.

Expanded PTFE (ePTFE) is particularly preferred as the porous material because of its low auto-fluorescence as well as for its chemical inertness and high temperature stability. Methods for making ePTFE are described in U.S. Pat. No. 3,953,566 to Gore. Expanded PTFE is a microporous form of PTFE consisting of irregular shaped pores. Whereas the exceptionally high surface area to volume ratio of microporous expanded PTFE (ePTFE) suggests that it might serve well in this application, the irregular pore shape makes it an unlikely candidate. Surprisingly, however, the irregularity of the ePTFE structure, with its non-circular pores, does not compromise the performance; indeed, ePTFE is the most preferred porous material. The pores of expanded PTFE are created by an expansion-by-stretching process performed at elevated temperatures. Expansion creates a microporous structure in which nodes are interconnected by fine fibrils. Preferred ePTFE materials are made in accordance with the teachings of U.S. Pat. No. 4,187,390 to Gore.

The choice of pore size is a key factor in selecting the porous material. In order to be an effective microarray substrate, the pores must be small enough to inhibit lateral spreading of the solution during the spotting process. It is believed that if the pores are too large, the spotting liquid will spread in all directions and the spots will run into each other thereby leading to crosstalk and contamination. The spot to spot distance can be increased to avoid this problem, however, this compromises the number of spots that can be placed within a given area. On the other hand, the pores must be large enough to enable the bio-molecules to enter the pores and to allow reagents to enter and exit the pores freely during washing processes. Bubble point measurement is a standard technique to characterize the maximum pore size of porous materials.

Whereas most porous substrates can be used to create the high functional density substrate of the present invention, for microarray applications, the bubble point should be at least 0.007 MPa (1 psi), preferably at least 0.070 MPa (10 psi). Preferred ePTFE materials possess bubble point values of at least 0.070 MPa (10 psi). Most preferably, the ePTFE material has bubble point values of at least 0.207 MPa (30 psi).

The microstructure of microporous ePTFE material consists of nodes interconnected by fibrils and can be characterized by its average fibril length. The fibril length can be measured by taking a scanning electron micrograph of the surface of the ePTFE membrane at reasonably high magnification (such as at 20,000×) and then measuring the length of the fibrils between the nodes. Thirty such measurements are taken of fibrils and the average fibril length is reported as the average of these measurements. Larger average fibril lengths are typically associated with lower bubble point and higher mean flow pore size. For the preferred ePTFE materials, it is believed that the average fibril length should be between 0.5 to 5 µm, preferably between 0.5 to 3 µm and most preferably between 0.5 to 2 µm.

The high functional site density substrate of this invention can be formed by using a porous material ranging in thickness from 5 µm and above. Increased thickness provides higher internal surface for attachment of functional groups thereby leading to increased functional density. For microarray applications, however, there is a limit to the thickness of the porous material. An excessively thick material is not desirable since such a material may absorb excessive amounts of probe solution during contact printing thereby causing the printing pins to rapidly become dry, thus affecting the spot clarity. In addition, excessively thick materials are difficult to process particularly during the washing step after hybridization. Inadequate washing of the hybridization liquids from the material can lead to residual reagents causing increased auto-fluorescence of the substrate. For a microarray substrate, the preferred thickness of the porous material is about 250 µm or less, most preferably about 125 µm or less.

The present invention relies on the internal surface of the porous material to attach the functional group. Internal surface area is a function of the thickness and the specific surface area of the porous material. Expectedly, specific surface area is an important consideration for selection of the porous material. However, specific surface area is related to the pore size. Typically, the smaller the pore size, the greater the specific surface area. Consistent with pore size requirements, porous material with any specific surface area can be converted into a high functional site density of this invention. However, for a viable microarray substrate, the porous material should possess a specific surface area of at least 1 $m^2$/gm. The preferred ePTFE material has at least a 1 $m^2$/gm of specific surface area and most preferably at least 10 $m^2$/gm of specific surface area.

The porous material that can be used for the present invention is preferred to be free of any additives, particularly additives that can contribute to increased auto-fluorescence. However, if needed, the porous material can contain additives such as pigments, fillers, colorants, UV absorbers and the like.

The porous materials are converted into high functional density porous substrates of this invention by first depositing an intermediate layer of hydroxyl containing functional coating on the entire microstructure of the porous material and subsequently using organosilane chemistry to react with the hydroxyl group of the intermediate layer. Details of this conversion process are described below primarily for the preferred ePTFE material. However, the conversion method can similarly be applied to a large variety of porous materials described in the preceding sections.

Because of the inherent hydrophobicity of ePTFE, polar solutions such as microarray printing and hybridization buffers do not wet the substrate material. Also, due to the chemical structure of ePTFE, biomolecules such as nucleic acids or proteins do not efficiently bind to the material. Consequently, for effective binding of biomolecules, the ePTFE surface must be modified and functional groups need to be subsequently attached. Surface modification of ePTFE by coating its microstructure using organic polymers in order to render its surface hydrophilic has been described in U.S. Pat. Nos. 5,130,024 and 5,897,955 to Fujimoto and to Drumheller, respectively. Similar hydrophilic treatment of ePTFE using inorganic sol-gel formulations has been described in Japanese patent publication number 08-250101 and in U.S. Patent application 2004/0081886A1 to Zuckerbrod.

For the present invention, it is preferred that the surface modification be performed using low auto-fluorescing hydrophilic coatings that provide hydroxyl groups capable of subsequent reaction with silanes. Non-limiting examples of organic polymers that are suitable for such hydrophilic coatings are polyvinyl alcohol, polyethyleneglycol, polypropylene glycol, polyglycidol, poly(vinyl alcohol-co-ethylene), poly(ethyleneglycol-co-propyleneglycol), poly(ethyleneglycol-co-propyleneglycol), poly(vinyl acetate-co-vinyl alcohol, either alone or in combination. Optionally, these polymeric coatings can be covalently cross-linked to themselves in situ by using suitable cross-linking agents such as aldehydes, epoxides, anhydrides etc. Polyvinyl alcohol (PVOH) is the preferred organic polymer for the hydrophilic treatment of ePTFE. The optional cross-linking can be achieved by the use of aldehydes such as glutaraldehyde.

Sol-gel solution, as described below, is a more preferred solution inasmuch as it renders the ePTFE surface more amenable for subsequent functionalization by providing a larger number of hydroxyl groups. Sol-gel is a technique for preparing specialty metal oxide glasses and ceramics by hydrolyzing chemical intermediates or mixtures of chemical intermediates that pass sequentially through a solution state and a gel state before being dehydrated to a glass or ceramic. The details of the sol-gel treatment used to make ePTFE hydrophilic are described in the Japanese patent publication number 08-250101.

The preferred sol-gel coating solution is derived from tetraethylorthosilicate (TEOS), tetramethylorthosilicate, or a sol-gel coating derived from sodium silicate solution or a colloidal silica suspension. Sol-gel coating solution derived from TEOS is the most preferred. Hydrophilic coatings, described above, can also be used to surface modify other microporous materials including but not limited to those made from nylon, ultrahigh molecular weight polyethylene (UHMWPE), polypropylene, porous PTFE, PVDF, porous glass, and the like. The hydrophilic treatment of the ePTFE and other microporous materials can be achieved by a number of ways. Usually, this treatment is achieved by applying a solution of the organic polymer or the inorganic sol-gel to membranes by commonly known methods such as dip coating, spraying, spin coating, brushing, roller coating, or Meyer bar coating. Care must be taken to add only enough of the coating to render the surface hydrophilic while maintaining the porosity of the material. Adding excessive amounts of the hydrophilic coating also will increase the auto-fluorescence of the substrate.

The hydrophilic treatment step, described above, renders the ePTFE and other microporous materials hydrophilic by depositing a hydroxyl containing coating over the entire microstructure. In a subsequent step, the hydroxyl groups are reacted with low auto-fluorescing organosilanes to obtain the desired functional groups depending on the specific biomolecules to be attached. For example, if complementary DNA (cDNA) molecules are to be attached to the substrate, amine functionality is most suitable and such functionality can be introduced by reacting the hydrophilized ePTFE material with suitable straight or branched aminosilane, aminoalkoxysilane, aminoalkylsilane, aminoarylsilane. Examples of silanes that can be used are γ-aminopropyltrimethoxysilane, γ-aminopropyltriethoxysilane, N-(beta-aminoethyl)-γ-aminopropyltrimethoxysilane, N-(beta-aminoethyl)-γ-aminopropyltriethoxysilane. Such amine functionality can also be introduced through organosilane coupled dendrimers available from companies such as Dendritech, Inc. (Midland, Mich.). Using this approach, through selection of appropriate organosilanes, different reactive functional groups can be attached to the ePTFE substrates. For the same functional group, the placement of the functional group from the attachment site on the surface can also be controlled by the size of the linker molecule used in the organosilane selected. Non-limiting examples of reactive functional groups that can be attached are amines, epoxides, adehydes, carboxyls, anhydrides, hydroxyl, acrylates, methacrylates, esters, thiols, azides, sulfonates and phosphonates to name a few. If desired, more than one functional group can be deposited on the substrate by reacting a mixture of silanes with different organofunctional groups with the hydroxyl groups from the intermediate layer. The functional groups can be further reacted with other chemical reagents to create the desired functionality for the targeted end use. For example, epoxide groups can be further reacted with diols to recreate hydroxyl functionality or amine functional groups can be further crosslinked through use of maleimide—NHS based crosslinkers to create a functionality that can react with biomolecules possessing amine functionality such as antibodies.

The silane treatment can be achieved by treating the hydrophilic ePTFE material with a dilute solution of the silane in an organic solvent at low pH. Details of such silane treatment and the variety of silanes with different organofunctional groups and different linker size can be obtained from the brochure "Silane Coupling Agents: Connecting Across Boundaries" available from Gelest, Inc. of Morrisville, Pa. Similar information and chemicals are also available from other companies such as United Chemical Technologies (Bristol, Pa.), Dow-Corning (Midland, Mich.), and GE Advanced Materials (Wilton, Conn.). For the present invention, the silane treatment can be achieved through conventional liquid coating processes such as dip coating, spraying, spin coating, brushing, roller coating, or Meyer bar coating. Alternatively, the silane can be deposited on the membrane microstructure through vapor phase coating. Care must be taken to add only enough of the silane to functionalize the ePTFE while maintaining the porosity of the material.

The process of the present invention dramatically improves the functionality of a variety of membranes as evidenced by significantly improved amine density values which can be measured using assays familiar to those skilled in the art. Most remarkably, treated ePTFE and other microporous membranes of the present invention exhibit well over an order of magnitude improvement in amine group density compared to prior art materials. Improvements to functionalized membranes of this magnitude were surprising and unexpected.

The functional group density can be measured in terms of moles of functional groups per unit superficial area of the substrate or per unit volume of the substrate. Using the inventive method, porous materials with amino group density ranging between 0 and 5 nanomoles/cm$^2$ were converted to substrates with functional group densities in the range of 50 to 1300 nanomoles/cm$^2$ depending on the specific chemical nature of the porous material. Given the thicknesses of these substrates, the functional density per unit volume translates to 2500 to 150,000 nanomoles/cm$^3$. For example, ePTFE and microporous PP materials which were devoid of any amino functionality were converted into amino functional substrates with amino functional density of 416 and 487 nanomoles/cm$^2$ using the inventive method. Since the inventive method generates functional sites by reacting different organosilanes with the hydroxyl groups deposited during the intermediate layer coating, the above functional group density values are not limited only to amine functional groups. Rather, the functional site density is expected to depend primarily on the density of hydroxyl groups resulting from the intermediate layer coating. It is therefore anticipated that through suitable choice of organofunctional silane compounds, functional site density greater than 50 nanomoles/cm$^2$ or greater than 2500 nanomoles/cm$^3$ can be achieved irrespective of the specific nature of the functional groups chosen.

Apart from use in microarray applications, the highly functional substrates of this invention can be used for effective binding and capture of a large variety of biomolecules in other applications such as in diagnostic devices, active filtration applications, blotting applications, and the like.

This remarkable increase in functional density of the substrate can be achieved while keeping auto-fluorescence quite low. This combination of high functional density and low auto-fluorescence is highly desirable in a microarray substrate since it maximizes the fluorescence signal from the hybridized target biomolecules over the background noise. The auto-fluorescence of the substrate can be determined by scanning the substrate prior to printing biomolecules using microarray scanners available commercially from several vendors such as Axon Instruments (Union City, Calif.) and Perkin-Elmer (Wellesley, Mass.). Scanning can be done at multiple wavelengths of interest, depending on the type of scanner used. Average fluorescence values can be calculated at the wavelengths of interest from the scanned substrate data. It should be noted that scanning can be performed at different instrument settings such as laser power, focus depth and PMT gain. Signal intensities are function of these settings. Therefore auto-fluorescence values should be accompanied by the scanner settings for a given instrument.

A GenePix 4000A scanner (Axon) was used to measure the auto-fluorescence of the substrates for this invention. The laser power and the focus depth of this scanner were fixed at 100% and 0 μm respectively, and all measurements were done at a PMT setting of 350. Using the method of this invention, for low fluorescence porous materials such as PTFE, UHMWPE, PP, glass, etc.; high functional density substrates can be made with auto-fluorescence level less than 1000 relative fluorescence units (RFU) and less than 100 RFU for the 532 nm (green) and 635 nm (red) wavelengths, respectively. In most cases the auto-fluorescence level of such high functional site density substrates can be much lower, typically less than 100 RFU and 30 RFU at 532 nm and 635 nm wavelengths, respectively.

The high functional density and low auto-fluorescence porous substrate is most suitable for microarray applications as it is expected to provide increased signal intensity over background noise. There are various ways such substrates can be used in microarray application. The substrate can be used as is or alternatively the substrate can be converted into a cassette or into the shape of a microscope slide through combining it with other plastic, ceramic or metallic parts through insert molding or other assembly techniques such ultrasonic bonding, RF welding, heat welding, or the like. By choosing the appropriate functionality, it is possible to attach large variety of biomolecules to the high functional site density substrate of this invention. Non-limiting examples of biomolecules that can be attached are nucleic acids, proteins, peptides, oligonucleotides, antibodies, cells, enzymes, and pathogens, to name a few.

For many applications, in order to ease both handling and printing, it is desirable to support the high density functional site substrate of this invention with a support layer. This support layer can be both flexible as well as rigid. The flexible support layer can be plastic films and metal foils. However, for traditional microarray application the support layer is typically rigid. Such rigid support layer can be made from a stiff material as long as the material maintains dimension stability at hybridization temperatures and does not get affected by the reagents used during printing, hybridization, washing and drying steps involved in typical microarray experiment. Non-limiting examples of materials that are suitable as the support layer are glass, metals, ceramics, and plastics. A glass microscope slide is most commonly used as the support layer.

In an embodiment of the present invention, the functional substrate may be adhesively bonded, at least partially, to the rigid support to create a composite microarray substrate. The resulting adhesive bond should be strong enough to survive processing steps of printing, hybridization, washing and drying steps involved with a typical microarray experiment. The adhesive therefore needs to possess the appropriate thermal and chemical resistance. It is also desired that the adhesive exhibits as low an auto-fluorescence level as possible. Typically, adhesives containing no conjugated bonds in their chemical structure are likely to demonstrate low auto-fluorescence. The adhesive chosen must bond well to the rigid support as well as to the functional porous layer. If needed, the support surface can be treated to enhance the bond with the adhesive. Treating the support surface with organosilane is an example of a surface treatment that can be used to enhance adhesion. Alternatively, adhesion-promoting additives such as silane coupling agents can be added to the adhesive to promote better bond between the adhesive and the rigid support. For acceptable bond to the functional porous substrate, the adhesive needs to penetrate into the porous structure. If the adhesive viscosity or surface tension is not low enough to allow this penetration, the adhesive can be solvated with low viscosity and/or low surface tension solvents to promote this penetration. However, caution must be exercised to ensure that the adhesive does not penetrate excessively into the cross-section of the functional substrate since this would reduce the availability of the functional groups as well as increase the auto-fluorescence level of the composite microarray substrate Various kinds of adhesive can be used. The adhesive can be thermosetting in nature. Examples of such adhesives include but are not limited to epoxies, acrylics, silicones. These types of adhesives can be applied either to the support layer or to the functional layer, contacted to the other surface to be bonded, and then cured through application of energy in the form heat, UV radiation or the like. TRA-BOND FDA2 available from Tra-Con, Incorporated (Bedford, Mass.) is an example of a two-part thermosetting epoxy that can be used. If the adhesive is in liquid form, it can be applied by a variety of commonly used methods such as spraying, brushing, roller coating, etc. If the adhesive is in the form of a partially cured film, it can be laminated through application of pressure and/or heat. The adhesive can also be pressure sensitive in nature and belong to different chemical families. Acrylics (e.g., 3M 9461P Adhesive transfer tape from 3M Corporation, St. Paul, Minn.) and silicones (e.g. Dow-Corning® MD7-4602 from Dow-Corning Corporation, Midland, Mich.) are commonly used pressure sensitive adhesives (PSAs). In this case, the adhesive is applied either to the support or the functional substrate and bonded to the other material through application of pressure and/or heat. If the adhesive is in liquid form, it is applied as indicated above, dried if necessary to remove any volatiles and then bonded to its counterpart. Finally, the adhesive can be thermoplastic. Examples of such adhesives with low fluorescing properties are fluoroplastics (Dyneon™ THV Fluorothermoplastic from Dyneon LLC, Oakdale, Minn.); eFEP™ from Daikin America, Inc., Orangeburg, N.Y.; Teflon® FEP (Dupont Fluoroproducts, Wilmington, Del.), Topas® cyclic olefin copolymers from Ticona, Chatham, N.J., to name a few. The film form of these materials can be used to bond the functional layer to the support layer through application of heat and pressure in a lamination step. If available in resin form, the thermoplastic material can be dissolved in a suitable solvent and applied as a thin layer on either the functional membrane or the support layer, dried to remove the volatiles and bonded to its counterpart. The porous material layer can be adhesively bonded to the support prior to functionalization and then the composite can be functionalized through the steps of hydrophilic treatment and silane treatment as discussed previously.

FIG. 1 shows an article 10 according to an exemplary embodiment of the present invention. A support layer 12 has an adhesive 14 disposed thereon. A microporous fluoropolymer, ePTFE, substrate layer 16 is attached to support layer 12 by adhesive 14.

Support layer 12 is any rigid surface capable of bonding to microporous fluoropolymer layer 16, with or without the use of an adhesive. Glass is preferred for support layer 12. The surface of support layer 12 is optionally treated before adhesive 14 (if used) and microporous fluoropolymer layer 16 are applied.

Figure 2A:
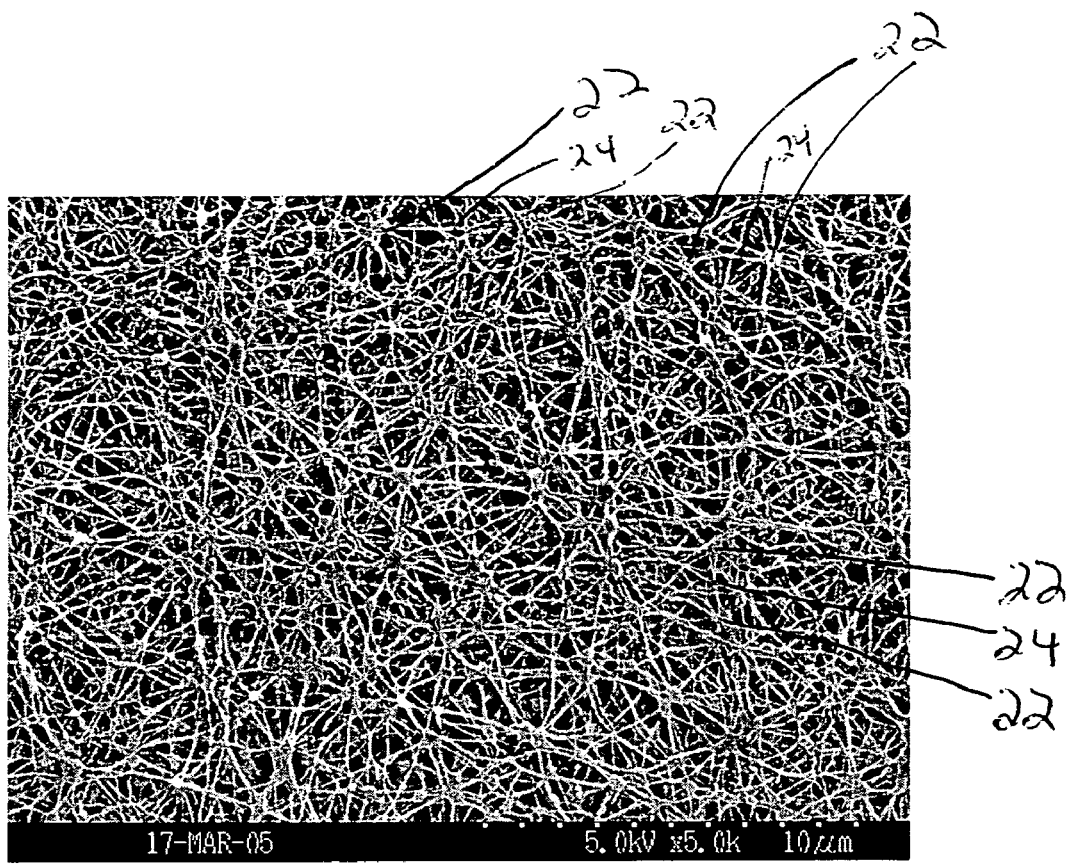
FIG. 2(A) is a scanning electron micrograph of the microporous surface of a microarray of an exemplary embodiment of the present invention prior to being functionalized.

A scanning electron micrograph of the surface 20 of the ePTFE material is shown in FIG. 2(A). This figure indicates the presence of nodes 22 interconnected by fibrils 24. The photomicrograph also depicts the irregular pores of this material.

Figure 2B:
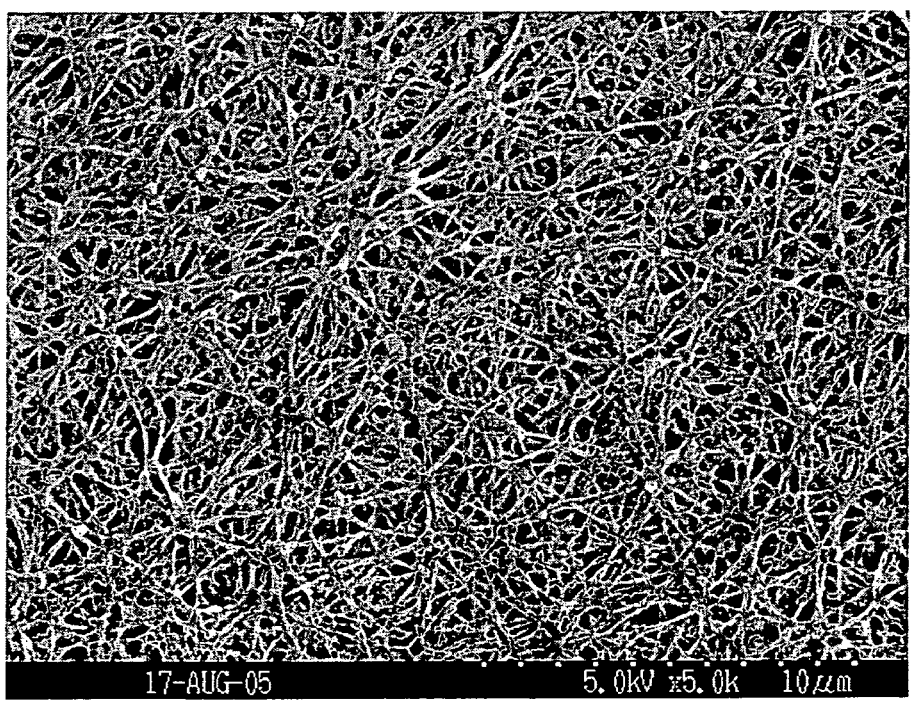
FIG. 2(B) is a scanning electron micrograph of the microporous surface of a microarray of an exemplary embodiment of the present invention subsequent to being functionalized.
Figure 2C:
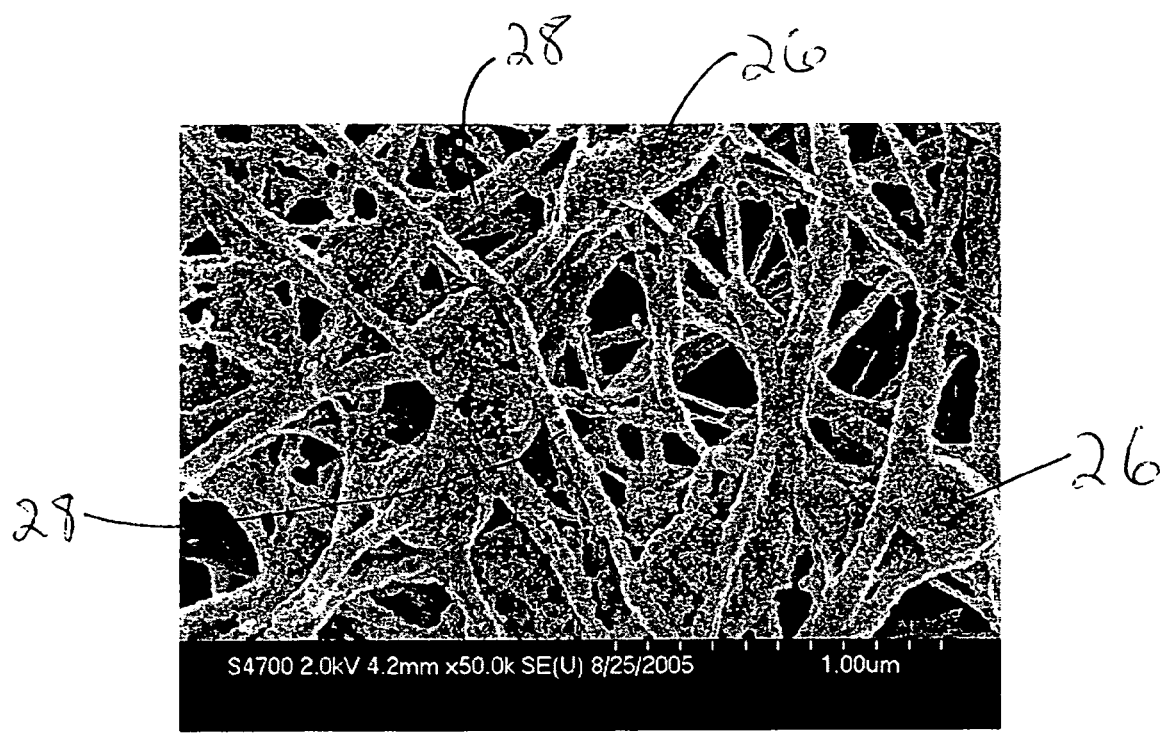
FIG. 2(C) is a scanning electron micrograph of the microporous surface of a microarray of an exemplary embodiment of the present invention subsequent to being functionalized.

A scanning electron micrograph of the surface of the porous substrate of this invention using ePTFE as the starting material is shown in FIGS. 2(B) and 2(C) at two different magnifications. The microstructure of the porous ePTFE materials was first treated with silica sol-gel to create an intermediate layer which was then reacted with an aminosilane. The coated nodes 26 and coated fibrils 28 of the microstructure are shown in FIG. 2(C).

Using the inventive method, composite microarray substrates employing the functional ePTFE layer were made that exhibit the desired features of unusually high functional group density and low auto-fluorescence. In particular, depending on the characteristics of the ePTFE, composite substrates can be made with functional group density of at least 50 nanomoles/cm$^2$, preferably of at least 100 nanomoles/cm$^2$ and most preferably of at least 250 nanomoles/cm$^2$. This is at least an order of magnitude higher than functional group densities obtained for prior art substrates. For example, depending on the specific characteristics of the ePTFE material used, the amine densities measured for the composite microarray substrates range from about 100 to 400 nanomoles/cm$^2$. In comparison, the amine densities measured for aminosilane treated non-porous glass slide (Corning Ultragaps™) and porous nylon membrane based Vivid™ microarray slide were about 4.8 and 6.5 nanomoles/cm$^2$ respectively.

While providing high functional site density, the inventive composite microarray substrate maintains its auto-fluorescence at a low level. The auto-fluorescence of the composite substrate can be determined by scanning the substrate prior to printing biomolecules using GenePix 4000A microarray scanner at a PMT setting of 350. Using the method of this invention, a composite microarray substrate comprising a functional ePTFE layer can be made with auto-fluorescence level less than 1000 relative fluorescence units (RFU) and less than 100 RFU for the 532 nm (green) and 635 nm wavelengths, respectively. In most cases the auto-fluorescence level of the composite microarray substrates can be much lower, typically less than 200 RFU and 30 RFU at 532 nm and 635 nm wavelengths, respectively.

The composite microarray substrate of this invention provides a versatile surface for immobilization of biomolecules. Other than its use in typical microarray analysis, the inventive substrate can also be used as a substrate with a variety of biomolecules attached to it in any arbitrary pattern. Examples of biomolecules that can be attached are nucleic acids, proteins, peptides, oligonucleotides, antibodies, cells, pathogens, to name a few.

The performance of the composite microarray substrate was determined by conducting an evaluation in which a DNA microarray was created using the composite substrate. The microarray was then hybridized with cDNA labeled with two fluorescent dyes, namely Cy3 and Cy5, that emit fluorescent signals at two different wavelengths. The fluorescent signals, at two different wavelengths, from each spot (and its vicinity) within the hybridized slides were then detected using a microarray scanner using a laser light source and a photo multiplier tube (PMT) as the detector. The scanner detects the fluorescent light intensities from the hybridized microarray substrate and the data is stored in the form of a scanned image of the substrate representing intensities on a color scale. The raw signal intensity data, thus obtained, were statistically analyzed using standard microarray data analysis software (such as GenePix® Pro from Axon Instruments, Genetraffic® from Lobion informatics or Scanarray® Express from Perkin-Elmer) to determine some key performance metrics such as signal to noise ratio and precision level. These performance criteria were determined for the composite microarray substrate of this invention as well as for substrates representing the prior art. Details of microarray data analysis are readily available in books such as "DNA Microarrays", edited by Ulrike A Nuber, Taylor & Francis, NY, 2005 or "Microarray analysis" by Mark Schena, John Wiley & Sons, Hoboken, N.Y., 2003.

Signal to noise ratio (SNR) is a key performance measure for a microarray substrate. The quality of the signal from a spot within a microarray depends on its intensity relative to its immediate surroundings, also known as local background noise. As the signal intensity from a spot approaches the intensity of the local background noise, the error in each measurement becomes potentially higher. At a given wavelength, the SNR for a spot can be easily computed by first determining the net signal intensity, which is the difference between the median signal intensity (S) for all pixels representing a spot and its median local background (B) for all pixels representing the immediate area just outside the spot. The background noise (NB) is estimated by calculating the standard deviation of the local background. SNR for the spot is then defined as:

$$SNR=(S-B)/NB$$

in which S, B, and NB are expressed in relative fluorescence units (RFU).

Typically, the SNR is determined for individual spots in an array. The average SNR (ASNR) is the average of all the SNR for individual spots in an array. Using microarray data analysis software, SNR calculations can be performed automatically for the large number of spots within a typical microarray.

High ASNR is always desired since it provides higher confidence in the accuracy of the data obtained from a microarray experiment. The composite microarray substrate of this invention provides remarkably high ASNR as compared to substrates of the prior art. In general, on average, the inventive composite substrate exhibits ASNR which is at least twice that obtained from aminosilane treated glass slides at both of the wavelengths. For example, the performance of a functionalized ePTFE membrane adhered to a glass slide far exceeds that of all prior art materials. It exhibits average signal to noise ratios for Cy5 and Cy3 of at least about 191 and 94, respectively. The most commonly used prior art slide exhibits signal to noise ratios for Cy5 and Cy3 of about 110 and 62, respectively It was surprising to notice that the composite microarray substrate of the present invention not only provides high ASNR, but was also very effective in stabilizing the fluorescent signal obtained. It is well known in the art that the signal from Cy5 dye is extremely unstable particularly under the influence of ozone. In fact, due to seasonal variation in ozone level in the ambient, it is not unusual to see the stability of the Cy5 signal deteriorate when the ambient ozone levels increase. It has now been found that the composite microarray substrate of this invention employing functional ePTFE layer is remarkably more effective in stabilizing the Cy5 signal as compared to that seen on substrates of the prior art. For example, in summer months when ambient ozone levels were high, the Cy5 SNR for the inventive substrate was about 7.7 times that of the Cy5 SNR on aminosilane treated glass slide and this ratio. Within 24 hours, this ratio increased to 38.9 as the Cy5 signal on the glass slide reduced drastically whereas the Cy5 signal was relatively more stable on the composite substrate of this invention.

In addition to high ASNR, precision is another performance measure that is highly desirable. In a microarray experiment, when the same target is labeled with two different fluorescent dyes (Cy3 & Cy5); it is expected that signals from both the wavelengths should provide the same information. In other words, if the Cy3 signal intensity is plotted against the Cy5 signal intensity on a graph with identical x and y axes, ideal data should lie on the 1:1 (or 45 degree) line. In reality, the data generally deviates from this line and the further this deviation is from the 1:1 line, the less reliable the data becomes. A measure of the precision of the data can be obtained by devising a measure of how close the data are to the 1:1 line. If there are M number of data points and out of that set if N data points lie outside the Z-fold up and Z-fold down boundaries, the Z-fold precision level can be defined as $$P_z=\text{Z-fold \% Precision level}=100\times(1-(N/M))$$

in which Z-fold up and Z-fold down boundaries represent relationships where the Cy3 signal intensity is Z times or 1/Z times that of the Cy5 signal intensity respectively. For example, 2-fold up implies that the Cy3 signal intensity is twice that of the Cy5 signal intensity and 2-fold down implies that the Cy3 signal intensity is half that of the Cy5 signal intensity. Higher $P_z$ values at lower Z levels indicate more precise and reliable data. The composite microarray substrate of the present invention exhibits remarkably high precision level. Typically, $P_{1.5}$ and $P_{1.2}$ were at least 99% and at least 90%, respectively, for the substrates of this invention. In comparison, respective values for aminosilane treated glass slide were 96 and 73%, respectively. Clearly, the composite substrate described here yields extremely precise and reliable data when used in a microarray experiment.

EXAMPLES

Test Methods

Thickness Measurement

Membrane thickness was measured by placing the membrane between the two plates of a Kafer FZ1000/30 thickness snap gauge (Käfer Messuhrenfabrik GmbH, Villingen-Schwenningen, Germany). The average of the three measurements was used.

Bubble Point Measurement

The bubble point and mean flow pore size were measured according to the general teachings of ASTM F31 6-03 using a Capillary Flow Porometer (Model CFP 1500 AEXL, Porous Materials Inc., Ithaca, N.Y.). The sample membrane was placed into the sample chamber and wet with SilWick Silicone Fluid (Porous Materials Inc., Ithaca, N.Y.) having a surface tension of 19.1 dynes/cm. The bottom clamp of the sample chamber had a 2.54 cm diameter, 3.175 mm thick porous metal disc insert (40 micron porous metal disk, Mott Metallurgical, Farmington, Conn.,) and the top clamp of the sample chamber had a 3.175 mm diameter hole. Using the Capwin software (version 6.62.1) the following parameters were set as specified in the table immediately below. The values presented for bubble point and mean flow pore size were the average of two measurements.

| Parameter | Set Point | Parameter | Set Point |
|---|---|---|---|
| maxflow (cc/m) | 200000 | mineqtime (sec) | 30 |
| bublflow (cc/m) | 100 | presslew (cts) | 10 |
| F/PT (old bubltime) | 40 | flowslew (cts) | 50 |
| minbppres (PSI) | 0 | eqiter | 3 |
| zerotime (sec) | 1 | aveiter | 20 |
| v2incr (cts) | 10 | maxpdif (PSI) | 0.1 |
| preginc (cts) | 1 | maxfdif (cc/m) | 50 |
| pulse delay (sec) | 2 | sartp (PSI) | 1 |
| maxpre (PSI) | 500 | sartf (cc/m) | 500 |
| pulse width (sec) | 0.2 | | |

Functional Group Density Measurement

A ninhydrin based assay was used to determine the density of the functional amino groups. The assay was based on the teachings of Sarin et. al. (Sarin, V. K., Kent, S. B. H., Tam, J. P. & Merrifield, R. B. (1981) Anal. Biochem. 117, 147-157). In this assay, ninhydrin was reacted with the substrates of this invention. The reaction product within the resulting liquid was sprectroscopically determined to arrive at the concentration of amine functionality. The assay used about 1 cm² size specimens obtained from the sample substrates and the following procedure was employed:

Reagent A—In a beaker, 40 g of phenol and 10 ml of absolute ethanol were mixed and warmed until a clear liquid was obtained. In a separate beaker, 0.042 g of potassium cyanide (KCN) was dissolved in 65 ml of water. Approximately 2 ml of this KCN solution was then diluted with 100 ml of absolute pyridine in a separate bottle. In a separate container labeled "Reagent A," 6 ml of the phenol/ethanol solution was mixed with 12.5 ml of the KCN/pyridine solution.

Reagent B—2.5 g of ninhydrin was dissolved in 10 ml of absolute ethanol.

Sample Analysis

In a test tube, 800 µl of Reagent A and 200 µl of Reagent B were added. The test tube was placed in a heating block set at 100° C. and the block was placed over a shaker. The shaker was run at 110 rpm for 10 min. The test tube was then removed and placed in a water bath. Ethanol was added to the tube until the total volume was 2 ml and the solution was well-mixed. 200 µl aliquots of this mix were pipetted into a glass 96 well plate and the absorbance at 570 nm was measured using a spectrophotometer.

Data Analysis

The amine density for each sample was calculated from the following relationship using the absorbance value after the blank absorbance was subtracted out.

$$\text{Amine Density (nanomoles/cm}^2\text{)} = [\text{Absorbance}_{sample} * \text{Volume(L)} * 10^9 \text{ (nmol/mol)}]/[\text{Ext. Co.}_{570} (M^{-1} cm^{-1}) * \text{Pathlength (cm)} * \text{Area}_{sample}(cm^2)],$$

in which Volume=2 ml=0.002 L, Ext. Co.=Extinction Coefficient=15,000 $M^{-1}$ $cm^-$, and the pathlength used was 0.4146 cm.

For each sample, three measurements were made and the amine density value was reported as the average of the three replicates.

In the case of unsupported functional substrates, the thickness of the substrate was directly measured. In this case, the functional group density was expressed as:

$$\text{Functional group density (nanomoles/cm}^3\text{)} = \text{functional group density (nanomoles/cm}^2\text{)/substrate thickness (cm)}$$

Auto-fluorescence Measurement

The auto-fluorescence of the unsupported substrates and the microarray slides prepared with these functionalized substrates was measured using an Axon Genepix 4000A (Axon Instruments Inc., Union City, Calif.) scanner with a PMT setting of 350 and a resolution of 10 µm. Auto fluorescence was measured at wavelengths of 635 nm and 532 nm. Slides samples (including rigid Vycor substrates) were placed in the slide holder with the substrate facing down and scanned for auto fluorescence. In the case of unsupported substrates such as membranes, the samples were draped around a plain glass microscope slide and placed in the slide holder with the substrate facing down and scanned for auto fluorescence. The scanned image was analyzed using GenePix Pro 5.0 software. Auto fluorescence values were recorded at 4800 discrete locations within the slide over a rectangular area. The top left corner of this area was 2.27 mm from the left edge and 12.21 mm from the top edge of the 25.4 mm×76.2 mm sample. The bottom right hand corner of this area was 18.04 mm from the left edge and 59.82 mm from the bottom edge of the sample. The average auto fluorescence values at the two wavelengths were reported for each sample slide and each substrate.

Signal to Noise Measurement

Signal to noise measurements of the microarray slides for the present invention were conducted by the Microarray Centre at University Health Network (UHN), Toronto, Canada. A 1718 clone set from the human genome was printed on the slide using a printing solution of the DNA in 3×SSC at a concentration of 0.2 µg/ml. The printed array was organized in 32 blocks arranged in 8 rows and 4 columns with a grid-to-grid distance of 4500µ. Within each grid, there were 120 features arranged in 10 rows and 12 columns. The feature size was 100 µm and the feature-to-feature distance was 200µ. Humidity level during printing was controlled between 55-60%. Following printing, the printed probes on the slide were dried at 95° C. for 1 minute and then cross-linked at 2500 micro Joules of power using a UV Stratalinker™ 1800 (Stratagene).

The following labeling protocol was used to generate labeled cDNA from 10 µg total RNA.

Reverse Transcription

In a 0.5 µl tube, combine 8.0 µl of 5× First Strand buffer (Superscript II, Invitrogen), 1.5 µl of AncT primer (5'-$T_{20}$VN, 100 pmol/µl), 3.0 µl of dNTP-dTTP (6.67 mM each of dATP, dCTP, dGTP), 3.0 µl of 2 mM dTTP, 3.0 µl of 2 mM AA-dUTP (Sigma, catalog no. A-0410), 4.0 µl of 0.1M DTT, 1.0 µl of control RNA (artificial Arabadopsis transcripts (2-10 ng/µl), optional), 0.1-10 µg of total RNA (0.1-0.5 µg mRNA or 5-10 µg total RNA), and 40 µl of nuclease-free water.

Incubate the labeling reaction at 65° C. for 5 minutes, then at 42° C. for 2 minutes (to partially cool solution). It is not necessary for the incubation to occur in the dark.

Add 2 µl reverse transcriptase (Superscript II, Invitrogen) and incubate at 42° c. for 2 hours.

Add 8 µl of 1M sodium hydroxide and heat to 65° C. for 15 minutes to hydrolyze RNA.

Add 8 µl of 1M hydrochloric acid and 4 µl of 1M tris-HCL, pH 7.5 to neutralize the solution.

Amino allyl-cDNA Purification

Purification was performed using CyScribe™ GFX™ Purification kit (GE Amersham, catalog no. 27-9606-02). Each sample was purified in one GFX column, using the following protocol.

Add 500 µl of capture buffer to each column.

Transfer cDNA product (approx 62 µl) to the column, pipette up and down several times to mix, spin at 13800×g for 30 seconds and discard flow-through.

Add 600 µl of 80% ethanol and spin at 1300 rpm for 30 seconds and discard flow-through; repeat this step for a total of 3 washes.

Spin the column for an additional 30 seconds to ensure all ethanol is removed.

Transfer the GFX column to a fresh tube and add 60 µl of 0.017 M sodium bicarbonate, pH 9.

Incubate the GFX column at room temperature for 1 minute.

Spin at 13800×g for 1 minute to elute purified labelled cDNA.

Use SpeedVac to completely dry sample. Resuspend in 7 µl nuclease-free water.\

Preparing Monofunctional Reactive Cyanine Dye & Labeling

Alexa 647/Alexa 555 fluors (Invitrogen) and Cy5/Cy3 (Amersham) were used in this study and both will be referred to as Cy5 & Cy3 respectively. The Alexa fluors are sold individually packaged. Add 3 µl of DMSO per tube to resuspend the dye. Add entire contents of the tube to each labeling reaction. The Cy dyes come in packages of 5 µl. Add 45 µl of DMSO to each tube. Again, 3 µl of the resuspended dye was added to each labeling reaction.

Add 3 µl dye to 7 µl aminoallyl-labelled cDNA, mix by pipetting up and down, and incubate in the dark at room temperature for 1 hour.

Add 4.5 µl of 4M hydroxylamine to quench non-conjugated dye. Incubate in the dark at room temperature for 15 minutes.

Purification of Fluorescent Labeled Probe

Add 35 µl water to each reaction to bring each reaction volume to about 50 µl.

Combine the Cy5 and Cy3-labelled samples that will be co-hybridized.

Add 500 µL of capture buffer to each column.

Transfer labelled-cDNA product (approx. 100 µL) to the column, pipette up and down several times to mix, spin at 13,800×g for 30 seconds and discard flow-through.

Add 600 µL 80% ethanol and spin at 13,800×g for 30 seconds and discard flow-through; repeat this step for a total of 3 washes.

Spin the column for an additional 30 seconds to ensure all ethanol is removed.

Transfer the GFX column to a fresh tube and add 60 µL elution buffer (provided with kit)

Incubate the GFX column at room temperature for 1 minute.

Spin at 13,800×g for 1 minute to elute purified fluor-labelled cDNA.

SpeedVac sample to dryness (on high heat; be careful not to over-dry) and resuspend in 5 µL nuclease-free water Hybridization A prehybridization step is not required.

Make enough solution for all your hybridizations—make 100 µl per slide and an additional 100 µl for pipetting error.

To each 100 µL of DIG Easy Hyb solution (Roche), add 5 µL of yeast tRNA (Invitrogen; 10 mg/ml) and 5 µL of calf thymus DNA (Sigma; 10 mg/ml). Incubate the mixture at 65° C. for 2 minutes and cool to room temperature.

Add 100 µl of the prepared hybridization solution to each pooled pair of Cy5 and Cy3-labelled cDNA (about 5 µL).

Mix the hybridization solution with the labelled-cDNA, incubate at 65° C. for 2 minutes, and cool to room temperature Place cover slip (24×60 mm, non-lifter slip) onto a reliable surface (the corner of a tip box works well) and pipette the hybridization mixture onto the cover slip. Lay the slide "array-side" down on top of the cover slip (do not actually put the slide down on the cover slip simply hold it on top of the cover slip until the slide is wetted enough to pick up the cover slip). Quickly flip the slide, with cover slip stuck to it, over so the cover slip is on top of the slide.

Carefully place the slide(s) into hybridization chamber(s). The hybridization chambers that we use are plastic microscope slide boxes containing a small amount of DIG Easy Hyb solution in the bottom (to keep a humid environment). Clean plain microscope slides are placed at every second or third slide position in the slide box to create rails or a platform onto which the hybridization arrays can be placed. Each hybridization chamber can hold two or three hybridization slides (depending on which direction the slides are placed). The lid is carefully placed onto the box and the box is then wrapped with plastic wrap.

Incubate on a level surface in a 37° C. incubator overnight (about 16-18 hours)

Washing

Remove the cover slip by quickly but gently dipping the array in 1×SSC (let the cover slip slide off gently; hold the slide at the bar-code end with forceps). Place the slide into a staining rack and place into a staining dish (Evergreen Scientific through Diamed cat# E/S258-4100-000) with fresh 1×SSC.

When all of the arrays have been removed from the hybridization chambers, wash for 3 sets of 15 minutes each at 50° C. in clean slide staining boxes containing prewarmed (at 50° C.) 1×SSC/0.1% SDS with gentle occasional agitation After the washes are complete, rinse the slides twice in room temperature 1×SSC (plunging 4-6 times) and then in 0.1×SSC Spin slides dry at 89×g for 5 minutes in a slide box lined with Whatman paper. Alternatively, slides can be dried in a 50 mL Falcon tube (and spun at 89×g for 5 min)

Arrays should be stored in the dark. It is recommended that arrays be scanned as soon as possible after they are washed (at least within two days). The hybridized slides of this invention were scanned using Scanarray™ 4000 scanner (Perkin Elmer, Wellesly, Mass.) at laser power setting varying between 65-75 and a PMT setting ranging from 50-55.

The TIFF images were quantified using ArrayVision v.8.0 (Imaging Research Inc.). The data and images were then loaded into GeneTraffic™ (Lobion Informatics) for normalization. The "Lowess, sub-grid" method was chosen for normalization in GeneTraffic™. Normalized intensity values were downloaded from the GeneTraffic™ database. The average S/N was calculated in Excel for each slide type. The standard deviation for each replicate was calculated in Excel for each slide type. Each spot appears twice on every array so even where only one array was tested there were 2 replicates to calculate the standard deviation of the S/N between them. Where more arrays were used the standard deviation of S/N was calculated across all the replicate arrays and the replicate spots (2 per array).

Signal to noise ratio was also measured for Ultragaps slides from Corning Life Sciences. The procedure was identical to that mentioned above except that less (80 µl) hybridization buffer was used. Also, scanning was performed at a different setting which was determined to be optimum for these slides. Specifically, the laser power setting used varied between 95 to 100 and the PMT setting ranged from 70-80.

Precision Level

Precision level measurements were performed using arrays that were labeled with the same sample of RNA in both the Cy5 and Cy3 channels. Ideally, all data points would fall exactly on a 45° line drawn through the origin on a scatter plot of normalized Cy3 signal intensity against normalized Cy5 signal intensity on a log-log plot for all the data points (M) on the slide. From this plot, the number of data points (N) that lie outside the Z-fold up and Z-fold down limits were determined. The Consistency or Specificity or Precision level is defined as Z-fold Precision Level, %=100×(1−(N/M))

Functionalized Substrate Examples

Sol-gel Solution

A precursor solution was prepared by allowing 40.7 parts tetraethoxysilane (Dynasil A made by Degussa Corporation, Parsippany, N.J.), 14.1 parts deionized water, 44.8 parts ethanol and 0.4 parts hydrochloric acid (37%) to react for 24 hours at 65° C. The solution was then cooled and stored in a freezer until further use.

Silane Solution

A silane solution was prepared by mixing 2 parts of aminopropyltriethoxysilane (A0750, United Chemical Technologies, Bristol, Pa.) to 98 parts of a 95/5 (w/w) mixture of ethanol/water. This solution was prepared just prior to use and was allowed to stand for at least 5 minutes prior to its use.

Example 1

This example describes a highly functional microporous substrate of the present invention obtained by starting with ePTFE as the porous material. The surprising advantages of the process and articles of the present invention are apparent when examining the substantial improvement of the treated versus the untreated membranes.

Material type: ePTFE

Membrane

An expanded polytetrafluoroethylene (ePTFE) membrane made in accordance with the teachings of U.S. Pat. No. 4,187,390 was obtained. The ePTFE membrane was about 74µ thick and had a bubble point of about 0.434 MPa (63 psi). Water beading on the surface of the membrane attested to its hydrophobicity.

Sol-gel Treatment

The ePTFE membrane was treated by mounting the membrane on embroidery hoops for ease of handling and then immersing the membrane in a solution obtained by diluting the sol-gel solution with equal amounts of ethanol by weight. After 5 minutes, the membrane was removed and immersed in deionized water for 5 minutes. Following the rinse step, the membrane was air dried and then heated at 150° C. for 5 minutes. At this stage the membrane was hydrophilic and water readily wet the membrane.

Aminosilane Treatment

The hydrophilic membrane was further treated with aminosilane to provide functional amino groups on its microstructure. This was accomplished by immersing the membrane in the silane solution for 5 minutes, then rinsing it in isopropyl alcohol (IPA) for 2 minutes and heating the membrane at 110° C. for 10 minutes. The membrane was silane treated again by repeating the identical steps of 5 minute immersion in silane solution, 2 minute rinse in IPA and heating at 110° C. for 10 minutes.

Final Membrane

The resulting functionalized ePTFE membrane was 34 µm thick and a ninhydrin assay indicated the amine density to be 416.4 nanomoles/cm$^2$ (or 121435 nanomoles/cm$^3$). The auto fluorescence of the functionalized ePTFE membrane was measured as 21.2 and 30.4 respectively at 635 nm and 532 nm. For comparison purposes, an identical but untreated ePTFE membrane was tested for the presence of any functional amino group using the ninhydrin assay; no amino groups were detected.

Example 2

This example also describes a highly functional microporous substrate of the present invention obtained by starting with ePTFE as the porous material. Example 1 was repeated except that PVOH was substituted for Sol-gel. Again, the article of the present invention performed much better than the untreated membrane of the same type as described in Example 1.

Material Type: ePTFE

PVOH Treatment

The ePTFE membrane used in Example 1 was treated by mounting the membrane in an embroidery hoop for ease of handling and then immersing the membrane in IPA for 5 minutes, then in deionized water for 2 minutes, then in 5 wt. % aqueous solution of polyvinyl alcohol (P1180, Spectrum Chemicals, Gardena, Calif.) for 10 minutes. The membrane was removed and immersed in deionized water for 10 minutes. Following the rinse step, the membrane was air dried overnight under ambient conditions and then heated at 110° C. for 10 minutes. At this stage the membrane was hydrophilic and water readily wet the membrane.

Aminosilane Treatment

The hydrophilic membrane was further treated with aminosilane to provide functional amino groups on its microstructure. This was accomplished by immersing the membrane in the silane solution for 5 minutes, then rinsing in isopropyl alcohol (IPA) for 2 minutes and heating the membrane at 110° C. for 10 minutes. The membrane was again silane treated by repeating the identical steps of 5 minute immersion in silane solution, 2 minute rinse in IPA and heating at 110° C. for 10 minutes.

Final Membrane

The resulting membrane was tested using the ninhydrin assay and the average density of the functional amino groups was detected to be 118.5 nanomoles/$cm^2$.

Example 3

This example describes a highly functional microporous substrate of the present invention obtained by starting with microporous nylon as the porous material. The surprising advantages of the process and articles of the present invention are apparent when examining the substantial improvement of the treated versus the untreated membranes.

Material Type: Microporous Nylon

Membrane

A commercial microporous nylon membrane with surface treatment (Hybond N+) was obtained from Amersham Biosciences Corp., Piscataway, N.J.

The membrane was about 150 μm thick and had a bubble point of about 12.5 psi. Ninhydrin assay indicated that the functional amino group density of the membrane as obtained from the vendor was 9.7 nanomoles/$cm^2$ (or 638 nanomoles/$cm^3$).

Sol-gel Treatment and Aminosilane Treatment

The membrane was functionalized using the steps outlined in Example 1.

Final Membrane

The resulting membrane was about 147 μm thick and possessed a functional group density of 1093 nanomoles/$cm^2$ (74199 nanomoles/$cm^3$). This marked increase in functional amino group density was a consequence of the method of the present invention.

Example 4

This example describes a highly functional microporous substrate of the present invention obtained by starting with a porous ultrahigh molecular weight polyethylene (UHMWPE) sheet as the porous material. The surprising advantages of the process and articles of the present invention are apparent when examining the substantial improvement of the treated versus the untreated membranes.

Material Type: Porous UHMWPE

Membrane

A commercial porous UHMWPE sheet (Porex 9619) was obtained from Porex Corporation, Fairburn, Ga. The sheet was about 1524 μm thick and its bubble point was determined to be about 0.009 MPa (1.3 psi).

Sol-gel Treatment and Aminosilane Treatment

The porous sheet was functionalized using the steps outlined in Example 1.

Final Membrane

The resulting sheet was about 1524 μm thick and the functional group density was 426.9 nanomoles/$cm^2$ (2801 nanomoles/$cm^3$). The auto-fluorescence of the functionalized UHMWPE sheet was measured as 31.1 and 107.2 RFU respectively at 635 nm and 532 nm. For comparison purposes, the commercially obtained porous UHMWPE sheet was tested for the presence of any functional amino group using the ninhydrin assay. The assay indicated that the functional amino group density of the membrane was 1.1 nanomoles/$cm^2$ (or 7.0 nanomoles/$cm^3$). The auto fluorescence of the commercially available UHMWPE sheet was measured as 23.9 and 48.7 RFU respectively at 635 nm and 532 nm. This marked increase in functional amino group density without significantly increasing the auto fluorescence level was due to the method of the present invention.

Example 5

This example describes a highly functional microporous substrate of the present invention obtained by starting with microporous polypropylene as the porous material. The surprising advantages of the process and articles of the present invention are apparent when examining the substantial improvement of the treated versus the prior art microporous polypropylene membranes.

Material Type: Microporous Polypropylene

Membrane

A commercial microporous polypropylene membrane (Polysep, 0.1μ, catalog no. M01WP320F5) was obtained from GE Osmonics Inc., Watertown, Mass. The membrane was about 86μ thick and its bubble point was determined to be about 0.135 MPa (19.6 psi).

Sol-gel Treatment and Aminosilane Treatment

The membrane was functionalized using the steps outlined in Example 1.

Final Membrane

The resulting membrane was about 74 μm thick and the functional group density was now 486.8 nanomoles/$cm^2$ (66087 nanomoles/$cm^3$). For comparison purposes, the commercially obtained microporous polypropylene membrane was tested for the presence of any functional amino group using the ninhydrin assay. The assay could not detect any functional amino groups on this membrane.

Example 6

This example describes a highly functional microporous substrate of the present invention obtained by starting with porous PTFE as the porous material. The surprising advantages of the process and articles of the present invention are apparent when examining the substantial improvement of the treated versus the untreated membranes.

Material Type: Porous PTFE

Membrane

A commercial porous polytetrafluoroethylene (PTFE) membrane (Mupor PM17Y) was obtained from Porex Corporation, Fairburn, Ga. The membrane was about 152 μm thick and its bubble point was determined to be about 0.044 MPa (6.4 psi).

Sol-gel Treatment and Aminosilane Treatment

The porous membrane was functionalized using the steps outlined in Example 1.

Final Membrane

The resulting membrane was about 152 µm thick and the functional group density was now 78.6 nanomoles/cm$^2$ (5158 nanomoles/cm$^3$). No ninhydrin assay was performed on the untreated membrane since no functional amino groups were expected to be present.

Example 7

This example describes a highly functional microporous substrate of the present invention obtained by starting with microporous polyvinylidenefluoride as the porous material. The surprising advantages of the process and articles of the present invention are apparent when examining the substantial improvement of the treated versus the untreated membranes.

Material Type: Microporous Polyvinylidenefluoride Membrane

Membrane

A commercial microporous polyvinylidenefluoride membrane (PVDF-Plus Transfer membrane, 0.22µ, catalog no. PV2HY320F5) was obtained from GE Osmonics Inc., Watertown, Mass. The membrane was about 152µ thick and its bubble point was determined to be about 0.135 MPa (19.6 psi).

Sol-gel Treatment and Aminosilane Treatment

The membrane was functionalized using the steps outlined in Example 1.

Final Membrane

The resulting membrane was about 154 µm thick and the functional group density was now 420.6 nanomoles/cm$^2$ (27146 nanomoles/cm$^3$). The auto-fluorescence of the functionalized PVDF membrane was measured as 173.4 and 526.5 RFU respectively at 635 nm and 532 nm. No ninhydrin assay was performed on the untreated membrane since no functional amino groups were expected to be present. The auto fluorescence of the untreated PVDF membrane was measured as 36.6 and 58.2 RFU respectively at 635 nm and 532 nm.

Example 8

This example describes a highly functional microporous substrate of the present invention obtained by starting with porous glass as the porous material. This example describes the use of porous glass as the substrate. The surprising advantages of the process and articles of the present invention are apparent when examining the substantial improvement of the treated versus the untreated substrates.

Material Type: Porous Glass

Substrate

Fabricated 25.4 mm×76.2 mm×1 mm thick rectangular slides made from Vycor 7930 porous glass were obtained from Advanced Glass & Ceramics, Holden, Mass.

Aminosilane Treatment

Following the teachings of prior art, the porous glass slide was functionalized using just the silane treatment steps specified in Example 1.

Sol-gel Treatment and Aminosilane Treatment

Another sample of the porous glass slide was also functionalized using both the sol-gel and aminosilane steps outlined in Example 1.

Final Substrates

The slide that was only silane treated showed an amino group density of 1169.6 nanomoles/cm$^2$ (or 12118 nanomoles/cm$^3$) and the auto fluorescence levels to be 23.9 and 93.7 RFU respectively at 635 nm and 532 nm. In comparison, the porous glass slide that was functionalized using the method of the present invention as outlined in Example 1 (i.e., treated with both sol-gel and aminosilane) indicated functional amino group density of 1311.7 nanomoles/cm$^2$ (or 13590 nanomoles/cm$^3$). The auto fluorescence of this slide was measured as 36.3 and 332 RFU respectively at 635 nm and 532 nm. The ninhydrin assay was not performed on the untreated substrate since no functional amino groups were expected to be present. The auto-fluorescence of the untreated porous glass slide was measured to be 23.1 and 39.4 RFU respectively at 635 nm and 532 nm.

Composite Microarray Substrate Examples

Comparative Examples

Commercially available microarray slides were obtained and analyzed for functional amino group density using the ninhydrin assay and for auto fluorescence levels. The slides from Corning, Telechem and Erie Scientific are all non-porous glass slides with aminofunctional surfaces. In comparison, the Vivid® Microarray slide from Pall Corp. is a microporous nylon polymer membrane adhesively bonded to a glass slide. Results for these commercial microarray slides are summarized in Table 1.

TABLE 1

| Name | Source | Amino Group Density, nanomoles/cm$^2$ | 635 nm - Avg. RFU | 532 nm - Avg. RFU |
|---|---|---|---|---|
| Ultragaps slide | Corning Life Sciences | 4.8 | 21 | 23.4 |
| Array-It Superamine 2 slide | Telechem International | 0.9 | 21 | 26.5 |
| Aminofunctional slide | Erie Scientific Company | 1.0 | — | — |
| Vivid Microarray slide | Pall Corporation | 6.5 | 33.5 | 176 |

Example 9

An ePTFE membrane was bonded to a glass slide, then functionalized.

Plain pre-cleaned glass microscope slides (VWR, catalog no. 48300) were treated with the silane solution described above by dipping the slides in the solution for 5 minutes, then rinsing them in IPA for 2 minutes and then heating them at 110° C. for 10 minutes. The silane treated slides were then bonded to an ePTFE membrane that was 74 µm thick having a bubble point of about 0.434 MPa (63 psi) and having an average fibril length of 1.2 µm. The bonding was performed by spraying a 40 wt. % solution of TRABOND FDA2 epoxy adhesive (Tar-Con Inc., Bedford, Mass.) in methyl ethyl ketene onto the silane-treated glass slides using an air-brush kit (McMaster-Carr, catalog no. 9546T13).

The adhesive treated slides were placed on top of the ePTFE membrane that was secured in an embroidery hoop. The adhesive was then cured for 60 minutes in a forced air oven set at 110° C. Following curing, the excess ePTFE membrane was trimmed off the glass slide using a razor blade. The resulting composite slide had a layer of ePTFE membrane attached to one its surfaces. The membrane surface was hydrophobic. A ninhydrin assay indicated that no functional amino groups were present. Auto fluorescence of the membrane surface was expected to be about 21 and 22 RFU respectively at 635 nm and 532 nm.

The composite slides were then place in a slide rack (Wheaton, catalog no. 900403) and the slides were treated with sol-gel by immersing them in the sol-gel solution diluted with equal parts in weight of ethanol. After 5 minutes of immersion, the slides were removed and rinsed in de-ionized water for 5 minutes. The rinsed slides were air dried and then heated at 150° C. for 5 minutes. At this stage, the ePTFE membrane was extremely hydrophilic as evidenced by the fact that it readily wet with water. These sol-gel treated slides were further treated by immersing them into the silane solution for 5 minutes, then rinsing in IPA for 2 minutes and then heating them in an oven set at 110° C. for 10 minutes. At this stage, the ePTFE membrane surface of the slide possessed amino functionality. A ninhydrin assay indicated the functional amino group density to be 338.6 nanomoles/cm$^2$. The auto-fluorescence level of the membrane surface of the slide was measured to be 22.7 and 191.2 RFU at 635 nm and 532 nm, respectively.

Comparing these results with those of the prior art presented in Table 1 demonstrates that the present invention provides a microarray slide with significantly higher functional amino group density while maintaining the auto fluorescence level comparable to porous polymer membrane based commercial products.

Example 10

Plain pre-cleaned glass microscope slides (VWR, catalog no. 48300) were wiped clean with acetone and then bonded to an ePTFE membrane that was 74 μm thick having a bubble point of about 0.434 MPa (63 psi) and having an average fibril length of 1.2 μm. The bonding was done by manually spraying a 40 wt. % solution of TRABOND FDA2 epoxy adhesive containing 1.8% (on epoxy solids) of 3-glycidoxypropoyltrimethoxysilane (G6720, United Chemical Technologies, Bristol, Pa.) in methyl ethyl ketone on the glass slides by using an air-brush kit (McMaster-Carr, catalog no. 9546T13) and then placing the adhesive treated slides on top of the ePTFE membrane mounted on an embroidery hoop and curing the adhesive in an air circulating oven at 80° C. for 18 hours. Following curing, the excess ePTFE membrane was manually trimmed from the glass slide using a razor blade. The resulting composite slide had a layer of ePTFE membrane attached to one surface. The membrane surface was hydrophobic and ninhydrin assay indicated that no functional amino groups are present. Auto fluorescence of the membrane surface is expected to be about 21 and 22 RFU at 635 nm and 532 nm respectively.

The composite slides were then placed in a slide rack (Wheaton, catalog no. 900403) and the slides were treated with sol-gel solution by immersing it in the sol-gel solution diluted with equal parts in weight of ethanol. After 5 minutes of immersion, the slides are removed and rinsed in de-ionized water for 5 minutes. The rinsed slides were air dried and then heated at 150° C. for 5 minutes. At this stage, the ePTFE membrane is extremely hydrophilic and readily wets out with water. These slides were further treated by immersing the sol-gel treated slides into the silane solution for 5 minutes, then rinsing in IPA for 2 minutes and then heating them at 110° C. for 10 minutes. At this stage, the auto-fluorescence level of the ePTFE membrane surface on the slide was measured to be 27.4 and 350.8 RFU at 635 nm and 532 nm, respectively.

Example 11

The composite microarray slide described in Example 10 was processed at UHN in December 2005 to determine the average signal to noise ratio. For comparison, Ultragaps microarray slides (Corning) were also processed at that time. A similar comparison was attempted using Vivid microarray slide (Pall Corp.) using the same protocol. However, it was not possible to print the complete array on these slides using the contact printing method used here.

Ambient ozone level is well known to have a significant effect on the stability of the signal in the Cy5 channel. Samples of the prior art that are measured in the summer months exhibit much lower signal to noise ratio values than identical samples measured in colder months. The previously described inventive (Example 9) and prior art samples of this example had also been tested in March of 2005.

The signal to noise data appear in Table 2.

TABLE 2

| Slide Description | Number of Slides Used | Average Signal to Noise Ratio, Cy5 | Average Signal to Noise ratio, Cy3 |
|---|---|---|---|
| inventive sample tested December. | 2 | 205.8 | 116.1 |
| UltraGaps sample tested December | 5 | 110.1 | 81.35 |
| inventive sample tested March | 2 | 191.5 | 93.7 |
| UltraGaps sample tested March | 2 | 87.8 | 40.2 |

This data demonstrates the significantly higher signal to noise ratio values for the inventive articles when compared against prior art articles tested in the same time frame. The data also indicate the seasonal influence on the performance of the slides. The Cy5 signals from the inventive microarray substrate show much less seasonal influence than those substrates representing the prior art. The invention sample shows about a 7% variance, while the conventional sample shows about a 25% variance. The inventive sample thus has enhanced stability (defined as less than 20%, and preferably less than 10%, variability under the above conditions).

Figure 3A:
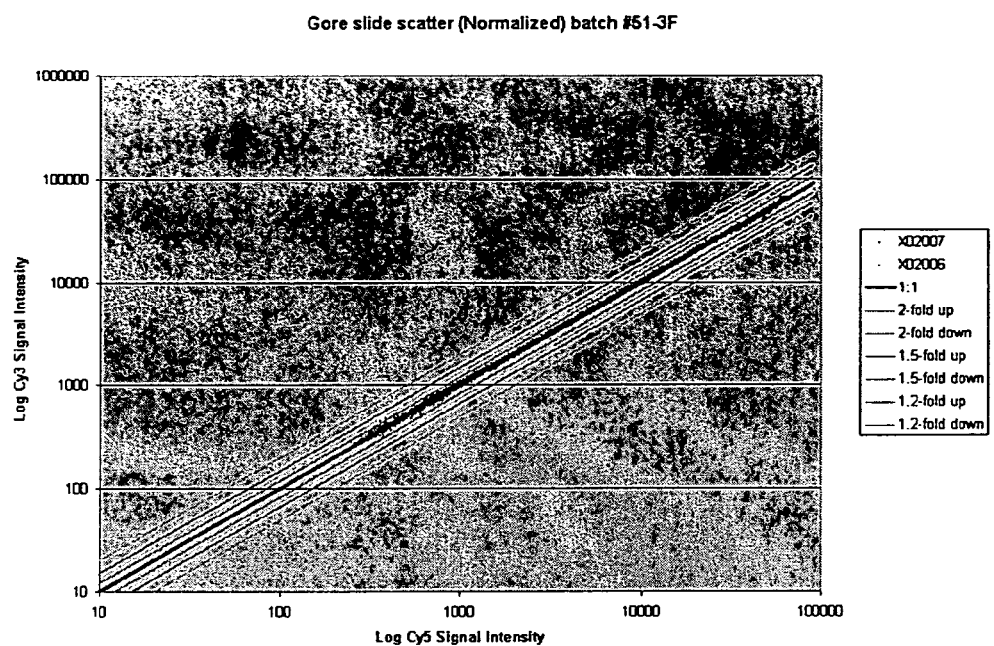
FIG. 3(A) is a scatter plot of normalized Cy3 and Cy5 signal intensity of microarrays using the substrate of an exemplary embodiment of the present invention.
Figure 3B:
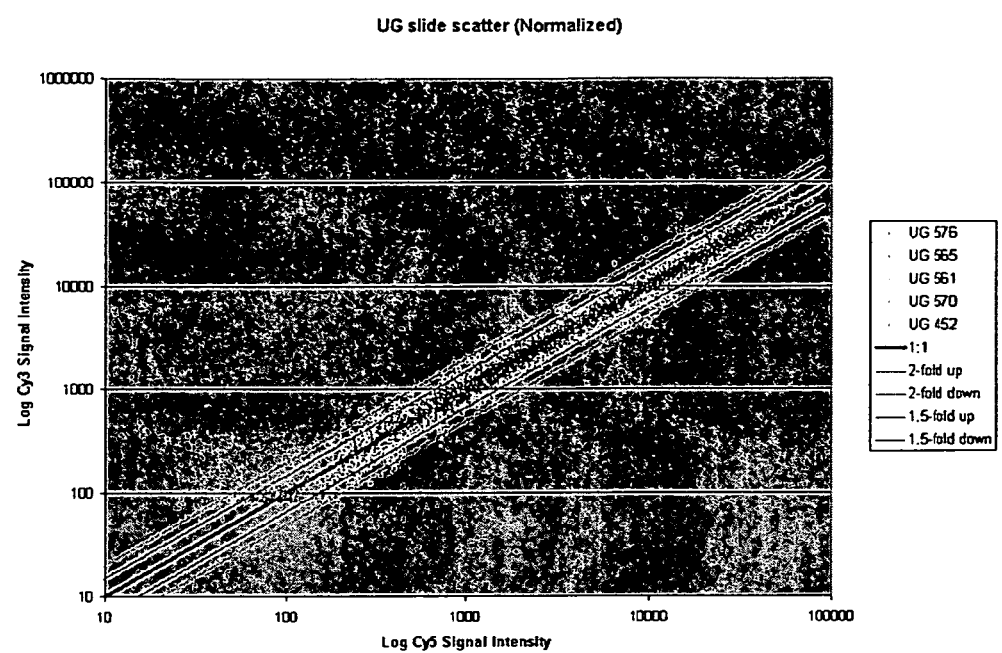
FIG. 3(B) is a scatter plot of normalized Cy3 and Cy5 signal intensity of microarrays using a substrate of the prior art.

The FIGS. 3(A) and 3(B) show the scatter plots for inventive and prior art (Ultragaps) samples of this example, respectively, that were tested in December 2005. Also shown in these figures are the 2-fold, 1.5 fold and 1.2 fold limits from which different precision levels were calculated. The precision level values are summarized in Table 3.

TABLE 3

| Slide Description | Number of slides Tested | $P_2$, 2-fold precision level, % | $P_{1.5}$, 1.5-fold precision level, % | $P_{1.2}$, 1.2-fold precision level, % |
|---|---|---|---|---|
| Inventive sample | 2 | 100 | 99.99 | 99.92 |
| prior art sample | 5 | 99.88 | 98.88 | 92.73 |

This data indicates that the microarray slides of the present invention yield significantly higher precision levels as fold limits are made smaller. That is, as the fold limits are made tighter, the precision level of the inventive article is seen to maintain its extremely high precision level, whereas the precision of the prior art article is seen to significantly decrease. Consequently, substrates of the present invention generate more useful data for a given microarray experiment compared prior art substrates. Also, the higher precision level afforded by the inventive substrate leads to higher degree of confidence in the microarray data, thereby requiring less test replication.

Example 12

Another composite microarray slide prepared as per the procedure described in Example 9 was processed at UHN in March 2005 to determine the average signal to noise ratio. In this case, a 7407 clone set for the mouse genome was used as the probe. For comparison, Ultragaps microarray slides (Corning) were also processed simultaneously. Signal to noise ratios were determined and the results are summarized in Table 4.

TABLE 4

| Slide Description | Number of Slides Used | Average Signal to Noise Ratio, Cy5 | Average Signal to Noise ratio, Cy3 |
|---|---|---|---|
| Inventive sample | 2 | 75.8 | 54.5 |
| UltraGaps sample | 2 | 34.5 | 34.1 |

The inventive microarray exhibited far higher signal to noise ratio for both wavelengths compared to microarrays of the prior art.

Scatter plots of normalized Cy5 and Cy3 signal intensity were also created for inventive and prior art (Ultragaps) samples of this example. The 2-fold, 1.5 fold and 1.2 fold limits were calculated from the scatter plots. The precision level values are summarized in Table 5.

TABLE 5

| Slide Description | Number of slides Tested | $P_2$, 2-fold precision level, % | $P_{1.5}$, 1.5-fold precision level, % | $P_{1.2}$, 1.2-fold precision level, % |
|---|---|---|---|---|
| Inventive sample | 2 | 99.98 | 99.91 | 97.87 |
| UltraGaps sample | 2 | 99.47 | 96.09 | 73.12 |

These data indicate that the microarray slides of the present invention yield significantly higher precision level as fold limits are made smaller. That is, as the fold limits are made tighter, the precision level of the inventive article is seen to maintain its extremely high precision level, whereas the precision of the prior art article is seen to significantly decrease. Consequently, substrates of the present invention generate more useful data for a given microarray experiment compared to prior art substrates. Also, the higher precision level afforded by the inventive substrate leads to higher degree of confidence in the microarray data, thereby requiring less test replication.

Example 13

The composite microarray slide prepared as per the procedure described in Example 9 was processed at UHN in June 2005 to determine the average signal to noise ratio. In this case, a 19008 clone set from human genome was used as the probe. For comparison, Ultragaps microarray slides (Corning) were processed simultaneously. In order to study the signal stability, the same slides were scanned on sequential days. The signal to noise ratios were determined and the results are summarized in Table 6.

TABLE 6

| | inventive sample | Inventive sample | Ultragaps sample | Ultragaps sample |
|---|---|---|---|---|
| Dye Type | Cy5 | Cy3 | Cy5 | Cy3 |
| Number of Slides Tested | 3 | 3 | 3 | 3 |
| Average S/N Ratio on Day 1 | 88.9 | 54.8 | 11.5 | 25.6 |
| Average S/N Ratio on Day 2 | 58.3 | 38.1 | 1.5 | 20.6 |
| Average S/N Ratio on Day 3 | 53.3 | 30.7 | 1.05 | 20.9 |

The data demonstrate that the microarray substrate of the present invention is significantly more effective in retaining the Cy5 signal over a longer time period.

The invention claimed is:

1. An article comprising a support layer adjacent to a polytetrafluoroethylene substrate comprising a porous microstructure having a fibril length between 0.5 and 5 microns and a thickness of about 125 microns or less, an interlayer over at least a portion of said microstructure and a functional layer attached to said interlayer, said functional layer having functional sites with a density of at least 50 nanomoles/cm$^2$.

2. An article as defined in claim 1 wherein said substrate is expanded polytetrafluoroethylene.

3. An article as defined in claim 2 wherein said expanded polytetrafluoroethylene has a fibril length between 0.5 and 5 microns.

4. An article as defined in claim 2 wherein said expanded polytetrafluoroethylene has a fibril length between 0.5 and 3 microns.

5. An article as defined in claim 2 wherein said expanded polytetrafluoroethylene has a fibril length between 0.5 and 2 microns.

6. An article as defined in claim 1 wherein said polytetrafluoroethylene substrate layer is about 75 microns thick.

7. An article as defined in claim 1 wherein said functional sites have a density of at least 100 nanomoles/cm$^2$.

8. An article as defined in claim 1 wherein said functional sites have a density of at least 200 nanomoles/cm$^2$.

9. An article as defined in claim 1 wherein said functional sites have a density of at least 250 nanomoles/cm$^2$.

10. An article as defined in claim 1 wherein said functional sites comprise amine groups.

11. An article as defined in claim 1 wherein said functional sites comprise hydroxyl groups.

12. An article as defined in claim 1 wherein said functional sites comprise carboxyl groups.

13. An article as defined in claim 1 wherein said functional sites comprise aldehyde groups.

14. An article as defined in claim 1 wherein said functional sites comprise epoxide groups.

15. An article as defined in claim 1 wherein said functional sites comprise thiol groups.

16. An article as defined in claim 1 wherein said functional sites comprise anhydride groups.

17. An article as defined in claim 1 wherein said functional sites comprise acrylate groups.

18. An article as defined in claim 1 wherein said functional sites comprise methacrylate groups.

19. An article as defined in claim 1 wherein said functional sites comprise ester groups.

20. An article as defined in claim 1 wherein said functional sites comprise azide groups.

21. An article as defined in claim 1 wherein said functional sites comprise sulfonate groups.

22. An article as defined in claim 1 wherein said functional sites comprise phosphonate groups.

23. An article as defined in claim 1 wherein said polytetrafluoroethylene substrate is attached to said support layer by an adhesive.

24. An article as defined in claim 1 wherein said polytetrafluoroethylene substrate is attached to said support layer by a thermosetting adhesive.

25. An article as defined in claim 1 wherein said polytetrafluoroethylene substrate is attached to said support layer by a thermoplastic adhesive.

26. An article as defined in claim 1 wherein said polytetrafluoroethylene substrate is attached to said support layer by a pressure sensitive adhesive.

27. An article as defined in claim 1 wherein said polytetrafluoroethylene substrate is attached to said support layer by an adhesive disposed over only a portion of said substrate or of said support layer.

28. An article as defined in claim 1 wherein said support layer comprises glass.

29. An article as defined in claim 1 wherein said support layer comprises quartz.

30. An article as defined in claim 1 wherein said support layer comprises stainless steel.

31. An article as defined in claim 1 wherein said support layer comprises plastic.

32. An article as defined in claim 1 wherein said article is a microarray substrate.

33. An article as defined in claim 1 further comprising an auto-fluorescence level less than about 1000 RFU at a wavelength of 532 nm.

34. An article as defined in claim 1 further comprising an auto-fluorescence level less than about 1000 RFU at a wavelength of 532 μm and a functional site density greater than 50 nanomoles/cm$^2$.

35. An article as defined in claim 1 further comprising an auto-fluorescence level less than about 100 RFU at a wavelength of 635 μm.

36. An article as defined in claim 1 further comprising an auto-fluorescence level less than 100 RFU at a wavelength of 635 μm and a functional site density greater than 50 nanomoles/cm$^2$.

37. An article as defined in claim 32 further comprising average signal to noise ratio for a Cy5 dye greater than 130.

38. An article as defined in claim 32 further comprising average signal to noise ratio for a Cy5 dye is greater than 150.

39. An article as defined in claim 32 further comprising average signal to noise ratio for a Cy3 dye is greater than 90.

40. An article as defined in claim 32 further comprising average signal to noise ratio for a Cy3 dye is greater than 110.

41. An article as defined in claim 32 further comprising a 1.5 fold precision level of at least 99% as calculated by the formula: Z-fold Precision Level, %=100×(1−(N/M)), from a scatter plot of normalized Cy3 signal intensity against normalized Cy5 signal intensity on a log-log plot.

42. An article as defined in claim 32 further comprising a 1.2 fold precision level of at least 76% as calculated by the formula: Z-fold Precision Level, %=100×(1−(N/M)), from a scatter plot of normalized Cy3 signal intensity against normalized Cy5 signal intensity on a log-log plot.

43. An article comprising a support layer adjacent to a polytetrafluoroethylene substrate comprising a porous microstructure having a fibril length between 0.5 and 5 microns and a thickness of about 250 microns or less, an interlayer over at least a portion of said microstructure and a functional layer attached to said interlayer, said functional layer having functional sites with a density of at least 50 nanomoles/cm$^2$, and a biomolecule attached to said functional sites.

44. An article as defined in claim 43 wherein said biomolecule is nucleic acid.

45. An article as defined in claim 43 wherein said biomolecule is protein.

46. An article as defined in claim 43 wherein said biomolecule is an oligonucleotide.

47. An article as defined in claim 43 wherein said biomolecule is a peptide.

48. An article as defined in claim 43 wherein said biomolecule is an antibody.

49. An article as defined in claim 43 wherein said biomolecule is an enzyme.

50. An article as defined in claim 43 wherein said biomolecule is a cell.

* * * * *

UNITED STATES PATENT AND TRADEMARK OFFICE
CERTIFICATE OF CORRECTION

PATENT NO. : 7,923,054 B2  
APPLICATION NO. : 11/407882  
DATED : April 12, 2011  
INVENTOR(S) : Dutta et al.

Page 1 of 1

It is certified that error appears in the above-identified patent and that said Letters Patent is hereby corrected as shown below:

At column 29, line 34: change "532 μm" to --532 nm--;

At column 29, line 38: change "635 μm" to --635 nm--; and

At column 29, line 41: change "635 μm" to --635 nm--.

Signed and Sealed this  
Thirteenth Day of September, 2011

David J. Kappos  
*Director of the United States Patent and Trademark Office*